United States Patent [19]
Weiner et al.

[11] Patent Number: 6,129,914
[45] Date of Patent: Oct. 10, 2000

[54] BISPECIFIC ANTIBODY EFFECTIVE TO TREAT B-CELL LYMPHOMA AND CELL LINE

[75] Inventors: George Weiner; Roger Gingrich, both of Iowa City; Brian K. Link, Carlville, all of Iowa; J. Yun Tso, Menlo Park, Calif.

[73] Assignee: Protein Design Labs, Inc., Fremont, Calif.

[21] Appl. No.: 08/397,411

[22] Filed: Mar. 1, 1995

Related U.S. Application Data

[63] Continuation-in-part of application No. 07/859,583, Mar. 27, 1992, abandoned.

[51] Int. Cl.$^7$ .................. A61K 39/395; C12P 21/04; C12P 21/08; C07K 16/00
[52] U.S. Cl. ..................... 424/133.1; 424/136.1; 435/70.21; 530/387.3; 530/388.1; 530/387.7; 530/388.75; 530/388.85
[58] Field of Search ...................... 435/70.21; 530/387.3; 424/133.1, 136.1

[56] References Cited

U.S. PATENT DOCUMENTS

| | | |
|---|---|---|
| 4,444,878 | 4/1984 | Paulus . |
| 4,658,019 | 4/1987 | Kung et al. . |
| 4,661,586 | 4/1987 | Levy et al. . |
| 4,676,980 | 6/1987 | Segal et al. . |
| 4,714,681 | 12/1987 | Reading . |
| 4,724,213 | 2/1988 | Epstein . |
| 4,831,117 | 5/1989 | Uckun . |
| 4,861,589 | 8/1989 | Ju . |
| 4,892,824 | 1/1990 | Skaletsky . |
| 5,582,996 | 12/1996 | Curtis ........................................ 435/7.1 |

FOREIGN PATENT DOCUMENTS

| | | |
|---|---|---|
| WO90/07861A | 7/1990 | WIPO . |

OTHER PUBLICATIONS

Brissinck, J. (1991) J. Immunol. 147(11):4019–4026.
Burgess et al (J. Cell Biol. 111:2129–2138), 1990.
Lazar et al (Mol & Cell Biol, 8: 1247–1252), 1988.
Tao (J. of Immunol, 143: 2595–2601), 1989.
Bowie et al (Science, 247: 1306–1310), 1990.
Manherimer–Lory et al (J. Exp. Med., 174:1639–1652), 1991.
Brissinck et al., "Bispecific antibodies in lymphoma," *Intern. Rev. Immunol.*, 10:187–194 (1993).
Fitzer–Schiller, *The Washington Post*, p. D3 (Jan. 19, 1993).
Gershon, *Nature*, 361:290 (1993).
R. Gingrich et al., "Identification and characterization of a new surface membrane antigen found predominantly on malignant b lymphocytes," *Blood*, 75(12):2375–2387 (Jun. 15, 1990).
M. Gravelle et al., "The targeting of cd4$^+$ t lymphocytes to a b cell lymphoma," *J. Immunol.*, 142(11):4079–4084 (Jun. 1, 1989).
Gregoriadis et al., *Trends in Biotech.*, 11:440–442 (1993).
Harris et al., *Trends in Biotech.*, 11:42–44 (1993).
Jung et al., "Induction of cytotoxicity in resting human t lyumphocytes bound to tumor cells by antibody heteroconjugates," *Proc. Natl. Acad. Sci. USA*, 84:4611–4615 (Jul., 1987).
Kung et al., "Monoclonal antibodies defining distinctive human t cell surface antigens," pp. 347–349 (Oct. 19, 1979).
Lanzavecchia et al., "The use of hybrid hybridomas to target human cytotoxic t lymphocytes," *Eur. J. Immunol.*, 17:105–111 (1987).
S. Moller et al., "Bispecific–monoclonal–antibody–directed lysis of ovarian carcinoma cells by activated human t lymphocytes," *Cancer Immunol. Immunother.*, 33:210–216 (1991).
T. Nitta et al., "Bispecific f(ab')$_2$ monomer prepared with anti–cd3 and anti–tumor monoclonal antibodies is most potent in induction of cytolysis of human t cells," *Eur. J. Immunol.*, pp. 1437–1441 (1989).
Oshimi et al., "Increased lysis of patient cd10–positive leukemic cells by t cells coated with anti–cd3 fab' antibody cross–linked to anti–cd10 fab' antibody," *Blood*, 77(5):1044–1049 (Mar. 1, 1991).
Segal et al., "Targeting of cytotoxic cells with hetero-crosslinked antibodies," *Cancer Investigation*, 6(1):83–92 (1988).
Songsivilai et al., "Bispecific antibody: a tool for diagnosis and treatment of disease," *Clin. Exp. Immunol.*, 79:315–321 (1990).
Staerz et al., "Hybrid antibodies can target sites for attach by t cells," *Nature*, 314:628–631 (Apr. 18, 1995).
Staerz et al., "Hybrid hybridoma producing a bispecific monoclonal antibody that can focus effector t–cell activity," *Proc. Natl. Acad. Sci. USA*, 83:1453–1457 (Mar., 1986).
Thorpe, *Trends in Biotech.*, 11:40–42 (1993).
Titus et al., "Human t cells targeted with anti–t3 cross–linked to antitumor antibody prevent tumor growth in nude mice," *The Journal of Immunology*, 138(11):4018–4022 (Jun. 1, 1987).
G. Weiner et al., "Bispecific Anti–idiotype/anti–cd3 antibody therapy of murine b cell lymphoma," *J. Immunol.*, 147:4035–4044 (Dec., 1991).

*Primary Examiner*—Paula K. Hutzell
*Assistant Examiner*—Susan Ungar
*Attorney, Agent, or Firm*—Townsend and Townsend and Crew

[57] ABSTRACT

The invention provides bispecific antibodies with selective cytotoxicity against malignant B-cells. The bispecific antibodies bind to an effector cell antigen and to a 28/32 kDa heterodimeric protein on the surface of malignant B-cells. The invention also includes the monospecific components of the bispecific antibodies, humanized versions thereof, and humanized bispecific antibodies. The invention further provides therapeutic and diagnostic methods employing these antibodies.

28 Claims, 14 Drawing Sheets

| | | | | | | | | | | | | | | | | | | |
|---|---|---|---|---|---|---|---|---|---|---|---|---|---|---|---|---|---|---|
| 1 | | D | I | Q | M | T | Q | S | P | S | S | L | S | A | S | V | G | D | R | V | T |
| 21 | | I | T | C | R | A | S | E | N | I | Y | S | Y | L | A | W | Y | Q | Q | K | P |
| 41 | | G | K | A | P | K | L | L | V | S | N | A | K | T | L | A | E | G | V | P | S |
| 61 | | R | F | S | G | S | G | S | G | K | Q | F | T | L | T | I | S | S | L | Q | P |
| 81 | | E | D | F | A | T | Y | Y | C | Q | H | H | Y | G | N | S | Y | P | F | G | Q |
| 101 | | G | T | K | L | E | I | K | R | T | V | A | A | P | S | V | F | I | F | P | P |
| 121 | | S | D | E | Q | L | K | S | G | T | A | S | V | V | C | L | L | N | N | F | Y |
| 141 | | P | R | E | A | K | V | Q | W | K | V | D | N | A | L | Q | S | G | N | S | Q |
| 161 | | E | S | V | T | E | Q | D | S | K | D | S | T | Y | S | L | S | S | T | L | T |
| 181 | | L | S | K | A | D | Y | E | K | H | K | V | Y | A | C | E | V | T | H | Q | G |
| 201 | | L | S | S | P | V | T | K | S | F | N | R | G | E | C |

FIG. 4C

| 1 | | Q | V | Q | L | Q | E | S | G | P | G | L | V | K | P | S | E | T | L | S | L |
|---|---|---|---|---|---|---|---|---|---|---|---|---|---|---|---|---|---|---|---|---|---|
| 21 | | T | C | T | V | S | G | F | S | L | T | N | Y | G | V | H | W | V | R | Q | S |
| 41 | | P | G | K | G | L | E | W | I | G | V | K | W | S | G | G | S | T | E | Y | N |
| 61 | | A | A | F | I | S | R | L | T | I | S | K | D | T | S | K | N | Q | V | S | L |
| 81 | | K | L | N | S | L | T | A | A | D | T | A | V | Y | Y | C | A | R | N | D | R |
| 101 | | Y | A | M | D | Y | W | G | Q | G | T | L | V | T | V | S | S | A | S | T | K |
| 121 | | G | P | S | V | F | P | L | A | P | S | S | K | S | T | S | G | G | T | A | A |
| 141 | | L | G | C | L | V | K | D | Y | F | P | E | P | V | T | V | S | W | N | S | G |
| 161 | | A | L | T | S | G | V | H | T | F | P | A | V | L | Q | S | S | G | L | Y | S |
| 181 | | L | S | S | V | V | T | V | P | S | S | S | L | G | T | Q | T | Y | I | C | N |
| 201 | | V | N | H | K | P | S | N | T | K | V | D | K | K | E | V | P | K | S | C | D |
| 221 | | K | T | H | T | C | P | P | C | K | C | P | A | G | G | R | I | A | R | L | E |
| 241 | | E | K | V | K | T | L | K | A | Q | N | S | E | L | A | S | T | A | N | M | L |
| 261 | | R | E | Q | V | A | Q | L | A | Q | K | V | M | N |

FIG. 4D

| | | | | | | | | | | | | | | | | | | | | |
|---|---|---|---|---|---|---|---|---|---|---|---|---|---|---|---|---|---|---|---|---|
| 1 | | Q | V | Q | L | Q | E | S | G | P | G | L | V | K | P | S | E | T | L | S | L |
| 21 | | T | C | T | V | S | G | F | S | L | T | N | Y | G | V | H | W | V | R | Q | S |
| 41 | | P | G | K | G | L | E | W | I | G | V | K | W | S | G | G | S | T | E | Y | N |
| 61 | | A | A | F | I | S | R | L | T | I | S | K | D | T | S | K | N | Q | V | S | L |
| 81 | | K | L | N | S | L | T | A | A | D | T | A | V | Y | Y | C | A | R | N | D | R |
| 101 | | Y | A | M | D | Y | W | G | Q | G | T | L | V | T | V | S | S | A | S | T | K |
| 121 | | G | P | S | V | F | P | L | A | P | S | S | K | S | T | S | G | G | T | A | A |
| 141 | | L | G | C | L | V | K | D | Y | F | P | E | P | V | T | V | S | W | N | S | G |
| 161 | | A | L | T | S | G | V | H | F | T | P | A | V | L | Q | S | S | G | L | Y | S |
| 181 | | L | S | S | V | V | T | V | P | S | S | S | L | G | T | Q | T | Y | I | C | N |
| 201 | | V | N | H | K | P | S | N | T | K | V | D | K | K | V | E | P | K | S | C | D |
| 221 | | K | T | H | T | C | P | P | C | P | A | P | E | L | L | G | G | P | S | V | F |
| 241 | | L | F | P | P | K | P | K | D | T | L | M | I | S | R | T | P | E | V | T | C |
| 261 | | V | V | V | D | V | S | H | E | D | P | E | V | K | F | N | W | Y | V | D | G |
| 281 | | V | E | V | H | N | A | K | T | K | P | R | E | E | Q | Y | N | S | T | Y | R |
| 301 | | V | V | S | V | L | T | V | L | H | Q | D | W | L | N | G | K | E | Y | K | C |
| 321 | | K | V | S | N | K | A | L | P | A | P | I | E | K | T | I | S | K | A | K | G |
| 341 | | Q | P | R | E | P | Q | V | Y | T | L | P | P | S | R | D | E | L | T | K | N |
| 361 | | Q | V | S | L | T | C | L | V | K | G | F | Y | P | S | D | I | A | V | E | W |
| 381 | | E | S | N | G | Q | P | E | N | N | Y | K | T | T | P | P | V | L | D | S | D |
| 401 | | G | S | F | F | L | Y | S | K | L | T | V | D | K | S | R | W | Q | Q | G | N |
| 421 | | V | F | S | C | S | V | M | H | E | A | L | H | N | H | Y | T | Q | K | S | L |
| 441 | | S | L | S | P | G | K | | | | | | | | | | | | | | |

| | | | | | | | | | | | | | | | | | | |
|---|---|---|---|---|---|---|---|---|---|---|---|---|---|---|---|---|---|---|
| 1 | D | I | Q | M | T | Q | S | P | S | S | L | S | A | S | V | G | D | R | V | T |
| 21 | I | T | C | S | A | S | S | S | V | S | Y | M | N | W | Y | Q | Q | K | P | G |
| 41 | K | A | P | K | R | L | I | Y | D | T | S | K | L | A | S | G | V | P | S | R |
| 61 | F | S | G | S | G | S | G | T | D | F | T | L | T | I | S | S | L | Q | P | E |
| 81 | D | F | A | T | Y | Y | C | Q | Q | W | S | S | N | P | P | T | F | G | G | G |
| 101 | T | K | V | E | I | R | K | T | V | A | A | P | S | V | F | I | F | P | P | S |
| 121 | D | E | Q | L | K | S | G | T | A | S | V | V | C | L | L | N | N | F | Y | P |
| 141 | R | E | A | K | V | Q | W | K | V | D | N | A | L | Q | S | G | N | S | Q | E |
| 161 | S | V | T | E | Q | D | S | K | D | S | T | Y | S | L | S | S | T | L | T | L |
| 181 | S | K | A | D | Y | E | K | H | K | V | Y | A | C | E | V | T | H | Q | G | L |
| 201 | S | S | P | V | T | K | S | F | N | R | G | E | C | | | | | | | |

FIG. 5C

| | | | | | | | | | | | | | | | | | | |
|---|---|---|---|---|---|---|---|---|---|---|---|---|---|---|---|---|---|---|---|
| 1 | Q | V | Q | L | V | Q | S | G | A | E | V | K | K | P | G | A | S | V | K | V |
| 21 | S | C | K | A | S | G | Y | T | F | I | S | Y | T | M | H | W | V | R | Q | A |
| 41 | P | G | Q | G | L | E | W | M | G | Y | I | N | P | R | S | G | Y | T | H | Y |
| 61 | N | Q | K | L | K | D | K | A | T | L | T | A | D | K | S | A | S | T | A | Y |
| 81 | M | E | L | S | S | L | R | S | E | D | T | A | V | Y | Y | C | A | R | S | A |
| 101 | Y | Y | D | Y | D | G | F | A | Y | W | G | Q | G | T | L | V | T | V | S | S |
| 121 | A | S | T | K | G | P | S | V | F | P | L | A | P | S | S | K | S | T | S | G |
| 141 | G | T | A | A | L | G | C | L | V | K | D | Y | F | P | E | P | V | T | V | S |
| 161 | W | N | S | G | A | L | T | S | G | V | H | T | F | P | A | V | L | Q | S | S |
| 181 | G | L | Y | S | L | S | S | V | V | T | V | P | S | S | S | L | G | T | Q | T |
| 201 | Y | I | C | N | V | N | H | K | P | S | N | T | K | V | D | K | K | V | E | P |
| 221 | K | S | C | D | K | T | H | T | C | P | P | C | K | C | P | A | G | G | L | T |
| 241 | D | T | L | Q | A | E | T | D | Q | L | E | D | K | K | S | A | L | Q | T | E |
| 261 | I | A | N | L | L | K | E | K | E | K | L | E | F | I | L | A | A | T | S | |

FIG. 5D

A—E—P—K—S—C—D—K—T—H—T—C—P—P—C—K—C—P—A—G—G—Zipper
———————— MODIFIED HUMAN IgG1 HINGE ————————

FIG. 10A

A—E—P—K—S—C—D—K—T—H—T—C—P—P—C—P—
———————— HUMAN IgG1 HINGE ————————

FIG. 10B

E—P—R—G—P—T—I—K—P—C—P—P—C—K—C—P—
———————— MOUSE IgG2a HINGE ————————

FIG. 10C

BISPECIFIC ANTIBODY EFFECTIVE TO TREAT B-CELL LYMPHOMA AND CELL LINE

CROSS-REFERENCE TO RELATED APPLICATION

This application is a continuation-in-part of U.S. Ser. No. 07/859,583 filed Mar. 27, 1992, now abandoned, which is incorporated by reference in its entirety for all purposes.

BACKGROUND OF THE INVENTION

Administration of monoclonal antibodies (MoAb) has shown promise as a new treatment modality for human malignancy. However, destruction of malignant cells by MoAb does not always occur, even after successful binding of the antibody to the target cell. A second approach to immunotherapy of malignancy involves the manipulation of the cellular immune system. Lymphokines, such as IL-2, can be used to activate both NK cells and T cells isolated from the blood, spleen, or malignant tumors themselves. The anti-tumor effects of such cells have been well documented both in vitro and in vivo. Toxicity of therapy based on IL-2 alone can be severe and may well limit the clinical utility of this therapy.

Immunotherapy of malignancy that attempts to combine the specificity of antibodies with the power of activated lymphocytes might be more effective and less toxic. One such approach is the use of bispecific antibodies to redirect activated T cell toxicity toward tumor cells expressing the target antigen (Ag.)

Various forms of bispecific antibodies have been produced. These include BSIgG, which are IgG molecules comprising two distinct heavy chains and two distinct light chains that are secreted by so-called "hybrid hybridomas", and heteroantibody conjugates produced by the chemical conjugation of antibodies or antibody fragments of different specificities.

Several investigators have evaluated anti-CD3/anti-tumor bispecific antibody structures as immunotherapeutic agents. Such studies have reported in vitro cytolysis of renal cell carcinoma, melanoma, glioma, lymphoma, leukemia and cells expressing the multidrug-resistance-related glycoprotein. IL-2-activated human peripheral lymphocytes directed by certain anti-CD3/anti-tumor-specific heteroantibody conjugates have also been reported to prevent the growth of human cancer xenografts in nude mice. Studies in vitro, and in vivo in immunodeficient mice bearing human xenografts have reported that certain bispecific antibodies are capable of blocking the growth of both tumor cells bearing certain target antigens and, to some extend, bystander tumor cells that are not recognized by the therapeutic antibody.

The cell membranes of lymphocytes are uniquely constructed and determine such diverse cellular phenotypic characteristics as the suppressor, inducer, or cytolytic function of the cell, the state of activation or stage of differentiation of the cell, and whether the cell belongs to a population that is monoclonal or polyclonal. The vast majority of cellular membrane antigens thus far described on malignant lymphocytes are represented on nonmalignant lymphocytes at some stage of differentiation or activation.

From the foregoing, it is apparent that a need exists for therapeutic agents that are targeted to an antigen found predominantly or exclusively on malignant cells, and which are capable of inducing strong cytolytic activity against such cells. The present invention fulfills this and other needs.

SUMMARY OF THE INVENTION

The present invention is premised on the realization that a bispecific monoclonal antibody which binds to malignant B-cell lymphomas and to T cells can be formed which effectively binds only to malignant B-cells and does not bind to normal B-cells.

Further, the present invention is premised on the realization that a bispecific antibody can be formed from a cell line obtained from peripherally diffuse large cell lymphoma to produce a monoclonal antibody that is specific only to malignant B-cells and that this monoclonal antibody can be modified to form a bispecific antibody which also binds to killer T cells or NK cells.

The present invention is further premised on the realization that a cell line formed from a fusion of cell lines which produces an IgG antibody specific to the T cells or NK cells and a cell line which produces the IgG antibody specific to B-cell malignancies in turn produce a unique bispecific antibody that effectively binds to both malignant B-cells and T cells or NK cells thereby effectuating the lysis or destruction of the malignant B-cells.

In the preferred embodiment the cell line is derived from the fusion of a cell line producing an antibody specific to the CD3 antigen of the T cell in combination with a cell line specific to a heterodimer on the cell membrane of the malignant B-cells as explained further below.

In a further aspect, the invention provides the 1D10 antibody, which is specific for the 28/32 kDa heterodimeric protein on the surface of malignant B-cells.

The invention further provides a humanized version of the 1D10 antibody. The humanized antibody comprises a humanized heavy chain and a humanized light chain. The humanized light chain comprises three complementarity determining regions (CDR1, CDR2 and CDR3) having amino acid sequences from the corresponding complementarity determining regions of the 1D10 immunoglobulin light chain, and a variable region framework from a human kappa light chain variable region framework sequence except in at least one position selected from a first group consisting of L48, L49, L69, and L70 wherein the amino acid position is occupied by the same amino acid present in the equivalent position of the 1D10 immunoglobulin light chain variable region framework. The humanized heavy chain comprising three complementarity determining regions (CDR1, CDR2 and CDR3) having amino acid sequences from the corresponding complementarity determining regions of 1D10 immunoglobulin heavy chain, and a variable region framework from a human heavy chain variable region framework sequence except in at least one position selected from a second group consisting of H27, H29, H30, H37, H67, H71, H78 and H83, wherein the amino acid position is occupied by the same amino acid present in the equivalent position of the mouse 1D10 immunoglobulin heavy chain variable region framework. The humanized antibody specifically binds the 28/32 kDa heterodimeric protein cells with a binding affinity having a lower limit of about $10^7$ $M^{-1}$ and an upper limit of about five-times the binding affinity of the 1D10 immunoglobulin. Preferably, the humanized light chain variable region framework is from the R3.5H5G antibody. In this case, position L43 can be substituted with the amino acid present in the equivalent position of a human kappa subgroup I consensus sequence. Preferably, the humanized heavy chain is from the heavy chain region variable framework of the IC4 antibody. In this case, position H73 can be substituted by the same amino acid present in the equivalent position of a human immunoglobulin subgroup II or IV consensus sequence.

In a further aspect, the invention provides humanized antibodies specific for the CD3 antigen. The antibodies comprise humanized heavy and light chains. The humanized light chain comprises three complementarity determining regions (CDR1, CDR2 and CDR3) having amino acid sequences from the corresponding complementarity determining regions of the M291 immunoglobulin light chain, and a variable region framework from a human kappa light chain variable region framework sequence. The humanized heavy chain comprises three complementarity determining regions (CDR1, CDR2 and CDR3) having amino acid sequences from the corresponding complementarity determining regions of M291 immunoglobulin heavy chain, and a variable region framework from a human heavy chain variable region framework sequence except in at least one position selected from a second group consisting of H30, H67, H68, H70, H72 and H74 wherein the amino acid position is occupied by the same amino acid present in the equivalent position of the mouse M291 immunoglobulin heavy chain variable region framework. The immunoglobulin specifically binds to a CD3 antigen on the surface of T cells with a binding affinity having a lower limit of about $10^7$ $M^{-1}$ and an upper limit of about five-times the binding affinity of the M291 immunoglobulin. Preferably, the humanized light chain variable region framework is from the light chain variable region framework of the HF2-1/17 antibody in subgroup I. Preferably, the humanized heavy chain region framework is from the heavy chain region variable framework of the 21/28 antibody. In this case, position H44 can be substituted with the same amino acid present in the equivalent position of a human immunoglobulin subgroup I consensus sequence.

In a further aspect, the invention provides humanized bispecific antibodies comprising a first binding fragment that specifically binds to the CD3 antigen and a second binding fragment that specifically binds to the 28/32 kDa heterodimeric antigen on the surface of the malignant B cells. The first binding fragment comprises a humanized form of the heavy chain variable region of the M291 antibody and a humanized form of the light chain variable region of the M291 antibody. The second binding fragment, which is linked to the first binding fragment, comprising: a humanized form of the heavy chain variable region from the 1D10 antibody and a humanized form of the light chain variable region from the 1D10 antibody.

Preferably, the first and second binding fragments each further comprises a segment of a constant region fused to the respective heavy chain variable regions, and the binding fragments are linked by association of the constant regions. For, example, the binding fragments can be Fab or Fab'. When both binding fragments are Fab', the bispecific antibody is a F(ab')$_2$. Optionally, the first and second binding fragments further comprise first and second leucine zippers fused to the respective constant regions.

The invention further provides pharmaceutical compositions comprising the antibodies described above. Also provided are methods of treating patients suffering from malignant B-cells employing a therapeutically effective amount of bispecific antibody as described above.

BRIEF DESCRIPTION OF THE DRAWINGS

FIG. 4. Amino acid sequences of the light chain (A) (SEQ ID NOS. 1 and 2) and the heavy chain (B) (SEQ ID NOS. 3 and 4) variable regions of the humanized 1D10 antibody (upper lines) and mouse 1D10 antibody (lower lines), not including the signal sequences. The three CDRs in each chain are underlined Residues in the human framework that have been replaced with mouse amino acids or consensus human amino acids are doubly underlined. Amino acid sequences of the complete light chain and the heavy chain of the humanized 1D10 are showed in (C) (SEQ ID NO. 5) and (E) (SEQ ID NO. 7), respectively. The $V_L$ domain consists of residues 1-107, and the $C_K$ 108-214. The $V_H$ domain consists of residues 1-116, the $C_H1$ 117-214, the hinge 215-229, the $C_H2$ 230-339, and the $C_H3$ domain 340-446. Amino acid sequence of the Fd-Jun in the humanized F(ab'-zipper)$_2$ of 1D10 is shown in (D) (SEQ ID NO. 6). The $V_H$ domain consists of residues 1-116, the $C_H1$ domain 117-214, the modified hinge 215-234, and the Fos leucine zipper 235-273.

FIG. 5. Amino acid sequences of the light chain (A) (SEQ ID NOS. 8 and 9) and the heavy chain (B) (SEQ ID NOS. 10 and 11) variable regions of the humanized M291 antibody (upper lines) and mouse M291 antibody (lower lines), not including the signal sequences. The three CDRs in each chain are underlined. Residues in the human framework that have been replaced with mouse amino acids or consensus human amino acids are doubly underlined. Amino acid sequences of the complete light chain of the humanized M291 are showed in (C) (SEQ ID NO. 12). The $V_L$ domain consists of residues 1-106, and the human $C_K$ domain 107-213. Amino acid sequence of the Fd-Fos in the humanized F(ab'-zipper)2 of M291 is shown in (D) (SEQ ID NO. 13). The $V_H$ domain consists of residues 1-120, the $C_H1$ domain 121-218, the modified hinge 219-238, and the Fos leucine zipper 239-279.

FIG. 10. (A). The sequence of the modified human IgG1 hinge used in the hinge-zipper fusion. Two residues Lys-Cys (underlined) were inserted in the modified hinge. The fist Cys in this modified hinge forms disulfide bond with the light chain, and the last three Cys residues form inter-heavy chain disulfides. For comparison, hinge sequences of the human IgG1 (B) and the mouse IgG2a (C) are also shown. All three Cys residues in the mouse IgG2a hinge are used for inter-heavy chain disulfides. After the insertion of Lys-Cys, the modified hinge and the mouse IgG2a hinge have extensive sequence homology near the COOH-terminus.

DEFINITIONS

Figure 1:
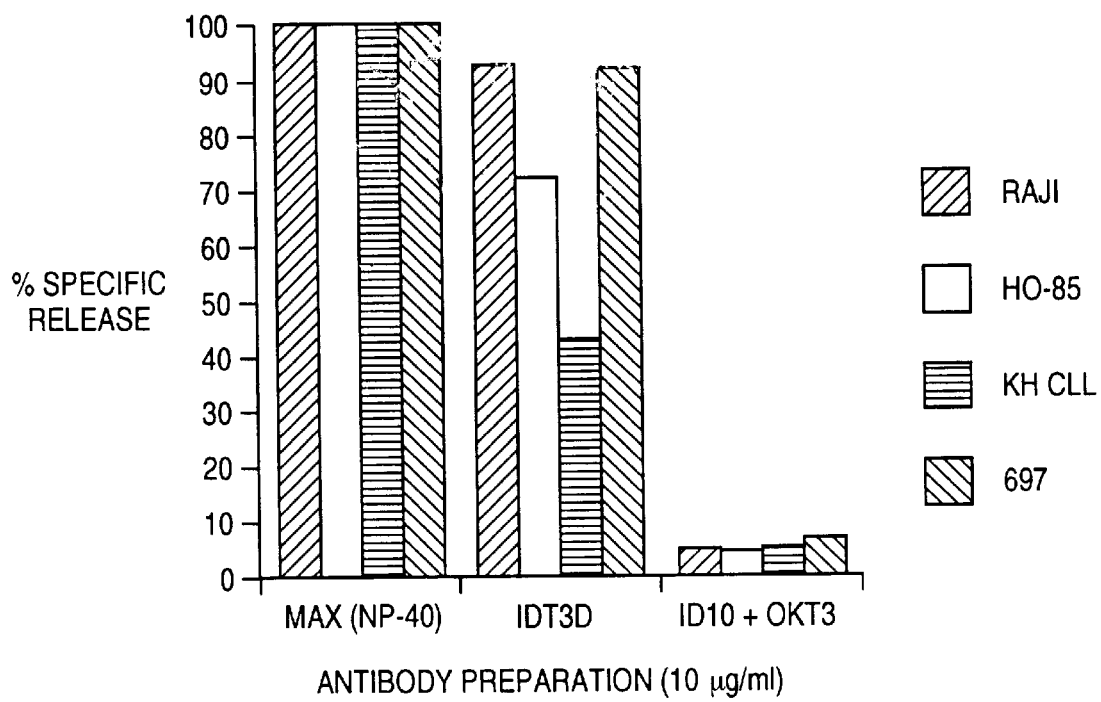
FIG. 1 is a graph depicting lysis of malignant B-cells by the bispecific antibody of the present invention.

The term "substantial identity" or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions which are not identical differ by conservative amino acid substitutions.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Amino acids from the variable regions of the mature heavy and light chains of immunoglobulins are designated Hx and Lx respectively, where x is a number designating the position of an amino acids according to the scheme of Kabat, *Sequences of Proteins of Immunological Interest* (National Institutes of Health, Bethesda, Md., 1987 and 1991). Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat. The use of the Kabat numbering system readily identifies amino acids at equivalent positions in different antibodies. For example, an amino acid at the L50 position of a human antibody occupies the equivalent position to an amino acid position L50 of a mouse antibody.

From N-terminal to C-terminal, both light and heavy chains comprise the domains FR1, CDR1, FR2, CDR2, FR3, CDR3 and FR4. The assignment of amino acids to each domain is in accordance with the definitions of Kabat (1987) and (1991), supra, or Chothia & Lesk, *J. Mol. Biol.* 196:901–917 (1987); Chothia et al., *Nature* 342:878–883 (1989).

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. The variable regions of each light/heavy chain pair form the antibody binding site. Thus, an intact antibody has two binding sites.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The term epitope includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

The term patient includes human and veterinary subjects.

DETAILED DESCRIPTION

The present invention provides bispecific antibodies, which are specific to both effector cells (T cells or natural killer cells) and to a 28/32 kDa heterodimeric antigen present on the surface of malignant B-cells. The present invention further provides hybridomas and other cells lines producing the claimed antibodies.

The 28/32 kDa antigen is found predominantly on the surface of malignant B lymphocytes and is not expressed on resting lymphocytes or B and T cells activated in vitro by a variety of inductive stimuli. See Gingrich et al., *Blood* 75, 2375–2387 (1990). The antigen can be expressed when lymphocytes undergo malignant transformation or, in some cases, when they are perturbed by the Epstein-Barr virus (EBV). Normal resting and stimulated lymphocytes do not express the antigen. The antigen is also absent on hemopoietic stem cells. Although the scientific basis for the 28/32 kDa antigen being expressed predominantly or exclusively on malignant B-cells is not critical to the practice of the invention, it is believed that the antigen may represent an aberrant post-translational processing variant of the HLA-Dr antigen.

To produce the antibodies specific to malignant B-cells, a lymphoma cell line derived from a patient with peripheralizing diffuse large cell lymphoma labeled HO-85 was grown in suspension culture RPMI 1640 with 10% fetal calf serum with a doubling time of approximately 24 hours. The cell line is CD20, mu, delta (weakly), kappa, HLA Class I and II antigen positive. It does not react with monoclonal antibodies detecting CALLA, T cell, myeloid or monocytic cell antigens. The cells react with the SFR7, DR7 and B7/21 monoclonal antibodies indicating that they express DR7 and DP antigens respectively.

Female BALB/c mice, age 6–10 weeks, were given 4 to 6 intraperitoneal inoculations at two week intervals with 5×10⁶ cells from the human large cell lymphoma line as described above. The animals were killed five days after last inoculation and the spleen cells were fused with the non-secretory murine myeloma cell line N-1. Hybridomas were selected in hypoxanthine-aminopterin-thymidine (HAT) medium after being plated in 96 well cell culture trays. After 10 days, 25 microliter aliquots were taken from each well for determination of malignant B-cell (anti-HO-85) antibody binding activity.

Malignant B-cell (anti-HO-85) antibody binding activity was determined by a whole cell, indirect radio immune assay using fresh HO-85 cells as targets. The identical assay was done using as targets RAJI (ATCC CCL86), MOLT-3 (ATCC CRL1582), HL-60 (ATCC CCL240) and fresh peripheral blood mononuclear cells. Wells that showed binding activity greater than 5 times that of tissue culture medium alone to HO-85 and Raji but were not reactive with MOLT-3, HL-60 and peripheral blood mononuclear cells were harvested.

Cells meeting the above criteria were found to produce an antibody referred to as 1D10 and were subsequently cloned by limiting dilution. The hybridoma grows well in vitro and ascites of pristine-primed BALB/c mice.

The portion of the malignant B-cells to which 1D10 binds is a heterodimeric polypeptide which contains two proteins with a molecular weight of the alpha and beta chains being 32 kDa and 28 kDa respectively. The proteins can be obtained by solubilizing malignant B-cells such as Raji cells with detergent. Molecular weight determination is made by using iodinated cells and single dimension SDS-PAGE analysis of the MoAb6-antigen precipitate. The formation of the 1D10 antibody is discussed by Gingrich et al., *Blood* 75, 2375–2387 (1990). Other antibodies having the same or similar binding specificity to 1D10 are screened by competition binding with 1D10 to the 28/32 kDa heterodimeric antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9, 242–253 (1983)); solid phase direct biotin-avidin EIA (see Kirkland et al., *J. Immunol.* 137, 3614–3619 (1986)); solid phase direct labeled assay, solid phase direct labeled sandwich assay (see Harlow & Lane, "Antibodies, A Laboratory Manual," Cold Spring Harbor Press (1988)); solid phase direct label RIA using I-125 label (see Morel et al., *Molec. Immunol.* 25, 7–15 (1988)); solid phase direct biotin-avidin EIA (Cheung et al., *Virology* 176, 546–552 (1990)); and direct labeled RIA (Moldenhauer et al., *Scand. J. Immunol.* 32, 77–82 (1990)). Typically, such an assay involves the use of cells bearing the 28/32 kDa antigen, an unlabelled test immunoglobulin and a labelled reference immunoglobulin (1D10). Competitive inhibition is measured by determining the amount of label bound to the cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The second component for the bispecific antibodies of the invention is an antibody having specificity for an antigen on the surface of T-cells or NK cells. Human T-cell antigens likely to be suitable include CD3, CD2, CD28, CD44, C69, A13 and G1. Suitable antigens on natural killer cells include FC Gamma receptors (3G8, B73.1, LEUL1, VEP13, and AT10). Human T-cell antigens that are probably unsuitable include MHC Class I, CD4, CD8, CD18 and CD71.

Cell lines producing IgG specific to the effector cell antigens described above are commercially available or can be produced de novo (see Example 3). The OKT3 cell (ATCC CRL 8001) is a suitable source of antibodies for the CD3 antigen. Other antibodies to the CD3 antigen include WT31, WT32, anti-leu-4, UCHT-1, SPV-3TA and SPV-T3B. The CD3 site is preferred because of its presence in all T cells.

The antibodies of the present invention can be produced by a cell line formed by the fusion of a first component cell line producing antibodies specific for the 28/32 kDa heterodimeric antigen with a second cell line which produces an antibody specific for either T cells or natural killer cells. For example, the hybridoma producing 1D10 was fused with OKT3 as follows.

The OKT3 hybridoma cell line was selected by growing OKT3 cells sequentially in media containing 0.13 mM 8-azaguanine, then 1.0 mM ouabain. Hybrid-hybridomas were produced by fusion (using 38% polyethylene glycol) of $10^6$ HAT resistant, ouabain sensitive, 1D10-secreting hybridomas with $10^6$ HAT sensitive, ouabain resistant OKT3-secreting hybridomas.

Fused cells were plated in HAT-ouabain media to select for hybrid-hybridomas. The HAT in this media prevented the growth of unfused OKT3 cells and the ouabain prevented the growth of unfused 1D10 cells. Thus, only hybrid-hybridomas containing genetic material from both parental hybridomas survived. Twelve hybrid-hybridomas were isolated using this technique.

Cell lines secreting bispecific antibodies can be identified by a three-step screening procedure. For example, in analysis of hybridomas formed from fusion of 1D10 and OKT3, an initial screen was performed in which hybrid-hybridoma supernatant was added to ELISA plates coated with goat anti-mouse IgG1 antibody. After washing, alkaline phosphatase labeled goat anti-mouse IgG2a was added. Reactivity indicated the hybrid-hybridoma supernatant contained single antibody molecules with both IgG1 and IgG2a heavy chains.

An indirect immunofluorescent assay was used as a second screen for all samples that were positive on ELISA. In this second screen, hybrid-hybridoma supernatant was added separately to HO-85 (1D10 reactive) and Jurkat (OKT3 reactive) cells. Goat anti-mouse IgG-FITC was added after washing to detect the presence of bound antibody. All twelve hybrid-hybridomas secreted antibody which was capable of binding to both HO-85 and Jurkat cells. One of these hybrid-hybridomas was selected for further study. It was subcloned by limiting dilution ×2, and designated 1DT3-D. This cell line was deposited on Mar. 24, 1992 under the Budapest Treat at the American Type Culture collection, 12301 Parklawn Drive, Rockville, Md. 20852 and assigned the number ATCC HB 10993.

1DT3-D was cultured in vitro in HB 101 media supplemented with 100 μg L-glutamine and 100 U/ml penicillin-streptomycin. These cells were transferred to a Mini Flo-path Bioreactor hollow fiber apparatus. Antibody obtained from spent media was fractionated by HPLC cation exchange using a gradient of 0.18 to 0.5M NaCl. The peak containing bispecific reactivity, as demonstrated by the above assays, was isolated, dialyzed against phosphate buffered saline, concentrated and used in further studies.

The bispecific antibody formed by fusion of 1D10 and OKT3 is a mouse derived monoclonal. Humanized versions of this antibody and other bispecific antibodies of the invention can also be employed as discussed in more detail below.

Humanized Antibodies

The invention further provides humanized immunoglobulins (or antibodies). Some humanized antibodies are specific for the T-cell antigen CD3. Other humanized antibodies are specific for the 28/32 kDa heterodimer on malignant B-cells. These humanized antibodies are useful as therapeutic and diagnostic reagents in their own right or can be combined to form a humanized bispecific antibody possessing both of the binding specificities of its components. The humanized forms of immunoglobulins have variable framework region(s) substantially from a human immunoglobulin (termed an acceptor immunoglobulin) and complementarity determining regions substantially from a mouse immunoglobulin (referred to as the donor immunoglobulin). The constant region(s), if present, are also substantially from a human immunoglobulin. The humanized antibodies exhibit a specific binding affinity for their respective antigens of at least $10^7$, $10^8$, $10^9$, or $10^{10}$ M$^{-1}$. Often the upper and lower limits of binding affinity of the humanized antibodies are within a factor of three or five or ten of that of the mouse antibody from which they were derived.

(1) Mouse Antibodies for Humanization

The starting material for production of humanized antibody specific for the 28/32 kDa heterodimer is preferably the 1D10 mouse antibody, although other mouse antibodies, which compete with 1D10 for binding to the 28/32 kDa heterodimer can also be used. A suitable starting material for production of humanized antibody specific for CD3 is the M291 antibody whose isolation is described in Example 3.

(2) Selection of Human Antibodies to Supply Framework Residues

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies.

Suitable human antibody sequences are identified by computer comparisons of the amino acid sequences of the mouse variable regions with the sequences of known human antibodies. The comparison is performed separately for heavy and light chains but the principles are similar for each.

(3) Computer Modelling

The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modelling. Computer hardware and software for producing three-dimensional images of immunoglobulin molecules are widely available. In general, molecular models are produced starting from solved structures for immunoglobulin chains or domains thereof. The chains to be modelled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modelled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

(4) Substitution of Amino Acid Residues

As noted supra, the humanized antibodies of the invention comprise variable framework region(s) substantially from a human immunoglobulin and complementarity determining regions substantially from a mouse immunoglobulin (e.g., 1D10 or M291). Having identified the complementarity determining regions of mouse antibodies and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modelling, examination of the characteristics of the amino acids at particular locations, or empirical observation of the effects of substitution or mutagenesis of particular amino acids.

When an amino acid differs between a mouse variable framework region and an equivalent human variable framework region, the human framework amino acid should usually be substituted by the equivalent mouse amino acid if it is reasonably expected that the amino acid:

(1) noncovalently contacts antigen directly, or (2) is adjacent to a CDR region or otherwise interacts with a CDR region (e.g., is within about 4–6 Å of a CDR region).

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in the mouse antibody can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, and alternative variant immunoglobulins are produced, one of which has that particular substitution, the other of which does not.

The humanized antibodies of the invention that are derived from the mouse 1D10 antibody usually contain a substitution of a human kappa light chain framework residue with a corresponding mu MAb 1D10 residue in at least 1, 2, 3 or 4 of the following positions: L48, L49, L69 and L70. The humanized antibodies also usually contain a substitution of a human heavy chain framework residue in at least 1, 2, 3, 4, 5, 6, 7, or 8 of the following positions H27, H29, H30, H37, H67, H71, H78 and H83. In preferred embodiments when the human light chain acceptor immunoglobulin is R3.5HG, the light chain also contains a substitution at position 43. This position is substituted with the amino acid from the equivalent position of a human immunoglobulin having a more typical amino acid residues or from a consensus sequence of such human immunoglobulins. Similarly, when the human heavy chain acceptor immunoglobulin is IC4, the heavy chain also contains a substitution at position 73.

The humanized antibodies of the invention that are derived from mouse M291 antibody contain no substitution of a human kappa light chain framework residue if the light chain acceptor is HF2-1/17. The humanized antibodies also usually contain a substitution of a human heavy chain framework in at least 1, 2, 3, 4, 5 and 6 of the following positions: H30, H67, H68, H70, H72 and H74. In preferred embodiments, when the heavy chain acceptor immunoglobulin is 21/28, the light chain also contains a substitution at position 44. This position is substituted with the amino acid from the equivalent position of a human immunoglobulin having a more typical amino acid residue or from a consensus sequence of such human immunoglobulin.

Usually the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

(5) Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. All nucleic acids encoding the antibodies described in this application are expressly included in the invention.

(6) Selection of Constant Region

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see Kabat et al., supra, and WO87/02671). Ordinarily, the antibody will contain both light chain and heavy chain constant regions. The heavy chain constant region usually includes CH1, hinge, CH2, CH3, and, sometimes, CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

(7) Expression Systems

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., *Proc. Natl. Acad. Sci. USA* 86, 10029 (1989); WO 90/07861; Co et al., *J. Immunol.* 148, 1149 (1992), which are incorporated herein by reference in their entirety for all purposes).

C. Fragments of Humanized Antibodies

The humanized antibodies of the invention include fragments as well as intact antibodies. Typically, these fragments compete with the intact antibody from which they were derived for antigen binding. The fragments typically bind with an affinity of at least $10^7$ $M^{-1}$, and more typically $10^8$ or $10^9$ $M^{-1}$ (i.e., within the same ranges as the intact antibody). Humanized antibody fragments include separate heavy chains, light chains Fab, Fab' F(ab')$_2$, and Fv. Fragments are produced by recombinant DNA techniques, or by enzymic or chemical separation of intact immunoglobulins.

Recombinant Bispecific Antibodies

The methods discussed above for forming bispecific antibodies from antibodies produced by hybridoma cells can also be applied or adapted to production of bispecific antibodies from recombinantly expressed antibodies such as the humanized versions of 1D10 and M291. For example, bispecific antibodies can be produced by fusion of two cell lines respectively expressing the component antibodies. Alternatively, the component antibodies can be co-expressed in the same cell line. Bispecific antibodies can also be formed by chemical crosslinking of component recombinant antibodies.

Component recombinant antibodies can also be linked genetically. In one approach, a bispecific antibody is expressed as a single fusion protein comprising the four different variable domains from the two component antibodies separated by spacers. For example, such a protein might comprise from one terminus to the other, the VL region of the first component antibody, a spacer, the VH domain of the first component antibody, a second spacer, the VH domain of the second component antibody, a third spacer, and the VL domain of the second component antibody. See, e.g., Segal et al., *Biologic Therapy of Cancer Updates* 2, 1–12 (1992).

In a further approach, bispecific antibodies are formed by linking component antibodies to leucine zipper peptides. See generally copending application 11823-003200 (Ser. No. 07/801,798, filed Nov. 29, 1991; Kostelny et al., *J. Immunol.* 148, 1547–1553 (1992) (incorporated by reference in their entirety for all purposes). Leucine zippers have the general structural formula (Leucine-$X_1$-$X_2$-$X_3$-$X_4$-$X_5$-$X_6$)$_n$ (SEQ ID NO. 14), where X may be any of the conventional 20 amino acids (*Proteins, Structures and Molecular Principles*, (1984) Creighton (ed.), W. H. Freeman and Company, New York), but are most likely to be amino acids with high α-helix forming potential, for example, alanine, valine, aspartic acid, glutamic acid, and lysine (Richardson and Richardson, *Science* 240, 1648 (1988)), and n may be 3 or greater, although typically n is 4 or 5. The leucine zipper occurs in a variety of eukaryotic DNA-binding proteins, such as GCN4, C/EBP, c-fos gene product (Fos), c-jun gene product (Jun), and c-myc gene product. In these proteins, the leucine zipper creates a dimerization interface wherein proteins containing leucine zippers may form stable homodimers and/or heterodimers.

The leucine zippers for use in the present invention preferably have pairwise affinity. Pairwise affinity is defined as the capacity for one species of leucine zipper, for example, the Fos leucine zipper, to predominantly form heterodimers with another species of leucine zipper, for example, the Jun leucine zipper, such that heterodimer formation is preferred over homodimer formation when two species of leucine zipper are present in sufficient concentrations. See Schuemann et al., *Nucleic Acids Res.* 19, 739 (1991). Thus, predominant formation of heterodimers leads to a dimer population that is typically 50 to 75 percent, preferentially 75 to 85 percent, and most preferably more than 85 percent heterodimers. When amino-termini of the synthetic peptides each include a cysteine residue to permit intermolecular disulfide bonding, heterodimer formation occurs to the substantial exclusion of homodimerization.

In the formation of bispecific antibodies, binding fragments of the component antibodies are fused in-frame to first and second leucine zippers. Suitable binding fragments including Fv, Fab, Fab', or the heavy chain. The zippers can be linked to the heavy or light chain of the antibody binding fragment and are usually linked to the C-terminal end. If a constant region or a portion of a constant region is present, the leucine zipper is preferably linked to the constant region or portion thereof. For example, in a Fab'-leucine zipper fusion, the zipper is usually fused to the C-terminal end of the hinge. The inclusion of leucine zippers fused to the respective component antibody fragments promotes formation of heterodimeric fragments by annealing of the zippers. When the component antibodies include portions of constant regions (e.g., Fab' fragments), the annealing of zippers also serves to bring the constant regions into proximity, thereby promoting bonding of constant regions (e.g., in a F(ab')2 fragment). Typical human constant regions bond by the formation of two disulfide bonds between hinge regions of the respective chains. This bonding can be strengthened by engineering additional cysteine residue(s) into the respective hinge regions allowing formation of additional disulfide bonds.

Leucine zippers linked to antibody binding fragments can be produced in various ways. For example, polynucleotide sequences encoding a fusion protein comprising a leucine zipper can be expressed by a cellular host or in vitro translation system. Alternatively, leucine zippers and/or antibody binding fragments can be produced separately, either by chemical peptide synthesis, by expression of polynucleotide sequences encoding the desired polypeptides, or by cleavage from other proteins containing leucine zippers, antibodies, or macromolecular species, and subsequent purification. Such purified polypeptides can be linked by peptide bonds, with or without intervening spacer amino acid sequences, or by non-peptide covalent bonds, with or without intervening spacer molecules, the spacer molecules being either amino acids or other non-amino acid chemical structures. Regardless of the method or type of linkage, such linkage can be reversible. For example, a chemically labile bond, either peptidyl or otherwise, can be cleaved spontaneously or upon treatment with heat, electromagnetic radiation, proteases, or chemical agents. Two examples of such reversible linkage are: (1) a linkage comprising a Asn-Gly peptide bond which can be cleaved by hydroxylamine, and (2) a disulfide bond linkage which can be cleaved by reducing agents.

Component antibody fragment-leucine zippers fusion proteins can be annealed by co-expressing both fusion proteins in the same cell line. Alternatively, the fusion proteins can be expressed in separate cell lines and mixed in vitro. If the component antibody fragments include portions of a constant region (e.g., Fab' fragments), the leucine zippers can be cleaved after annealing has occurred. The component antibodies remain linked in the bispecific antibody via the constant regions.

Therapeutic Methods

Pharmaceutical compositions comprising bispecific antibodies of the present invention are useful for parenteral administration, i.e., subcutaneously, intramuscularly and particularly, intravenously. The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the bispecific antibodies in these formulations can vary widely, i.e., from less than about 0.01%, usually at least about 0.1% to as much as 5% by weight and will be selected primarily based on fluid volumes, and viscosities in accordance with the particular mode of administration selected.

A typical composition for intravenous infusion can be made up to contain 250 ml of sterile Ringer's solution, and 10 mg of bispecific antibody. See *Remington's Pharmaceutical Science* (15th Ed., Mack Publishing Company, Easton, Pa., 1980).

The compositions containing the present bispecific antibodies or a cocktail thereof can be administered for prophylactic and/or therapeutic treatments. In therapeutic application, compositions are administered to a patient already affected by malignant B-cells (e.g., acute lymphoblastic leukemia, B-cell lymphoma, chronic lymphocytic leukemia and multiple myeloma) in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg of bispecific antibody per dose, with dosages of from 0.1 to 50 mg and 1 to 10 mg per patient being more commonly used. Single or multiple administrations on a daily, weekly or monthly schedule can be carried out with dose levels and pattern being selected by the treating physician.

In prophylactic applications, compositions containing the bispecific antibodies or a cocktail thereof are administered to a patient who is at risk of developing the disease state to enhance the patient's resistance. Such an amount is defined to be a "prophylactically effective dose." In this use, the precise amounts again depend upon the patient's state of health and general level of immunity, but generally range from 0.1 to 100 mg per dose, especially 1 to 10 mg per patient.

In some methods of treatment, bispecific antibodies are administered with a second agent (e.g., an interleukin) in an amount sufficient to active effector cells thereby augmenting their cytotoxicity to malignant B-cells compared with the administration of bispecific antibody alone. Interleukin-2 at a dosage of about 500,000 U/kg is suitable. Combination therapy is particularly appropriate when the bispecific antibody being administered is a F(ab')2 fragment.

The monospecific 1D10 antibody (particularly the humanized form) is also suitable for therapeutic administration to patients suffering from, or at risk of, B-cell malignancies. Optionally, the antibody is conjugated to a radiolabel or toxin. The monospecific M291 antibody (particularly the humanized form) can be used as an immunosuppressant in treatment of diseases and disorders of the immune system such as host vs. graft disease, graft vs. host disease, autoimmune diseases, and inflammation. See, e.g., Cosimi et al., *N. Engl. J. Med.* 305, 308 (1981); Russel et al., *Annu. Rev. Med.* 35, 63 (1984). The dosages and pharmaceutical excipients for administration of monospecific antibodies are similar to those for the bispecific antibodies.

Diagnostic Methods

The M291 and 1D10 antibodies (both mouse and humanized forms) are also useful in diagnostic methods. The 1D10 antibody (and other antibodies binding to the same or similar epitope) is useful for diagnosing the presence of malignant B cells and monitoring the efficacy of treatments thereto. The antibody is also useful for research purposes to identify and type cells of certain lineages and developmental origins. The M291 antibody is useful for diagnostic purposes in immunologically monitoring of patients (see, e.g., Cosimi et al., supra) and for research purposes in classifying leukocyte subtypes, e.g., as part of an antibody panel. Methods of diagnosis can be performed in vitro using a cellular sample (e.g., blood sample, lymph node biopsy or tissue) from a patient or can be performed by in vivo imaging.

EXAMPLE 1

The ability of 1DT3-D to induce the elimination of malignant B cells by T cells was evaluated in vitro. The assay used was a $^{51}$chromium-release cytotoxicity assay. Target malignant B cells ($10^7$ cells in 1 ml) were labeled during a 1 hour incubation with 100 $\mu$Ci $^{51}$Cr. T cells from normal donors were incubated in vitro with IL-2 or IL-2 and anti CD3 antibody for 3–7 days before use as effector cells. T cells were added to $^{51}$Cr-labeled malignant B cells along with antibody. This mixture was incubated for 4 hours, and cell free supernatant was removed and evaluated for the presence of released $^{51}$Cr by gamma counting. Maximum release was determined by evaluating supernatant obtained from wells that had been treated with detergent (NP-40) that induces the lysis of all cells. Background release was determined by evaluating $^{51}$Cr levels from samples that had target malignant B cells and T cells but no antibody. Specific release of $^{51}$Cr indicated lysis of the $^{51}$Cr-containing target cells, and was calculated using the following formula.

$$\frac{\text{Sample Release} - \text{Background Release}}{\text{Maximum Release} - \text{Background Release}} \times 100$$

FIG. 1 shows 1DT3-D induced the lysis of a large number of different malignant B cells including Raji (a cell line established from a patient with Burkitt's lymphoma), HO-85 (a large cell lymphoma cell line), 697 (a pre-B acute lymphoblastic leukemia cell line) and KH (fresh lymphocytes obtained from a patient with chronic lymphocytic leukemia). The T-cell target cell ratio was 10:1 and the antibody concentration was 5 $\mu$g/ml. Target lysis was not seen when monospecific antibody was used.

Figure 2A:
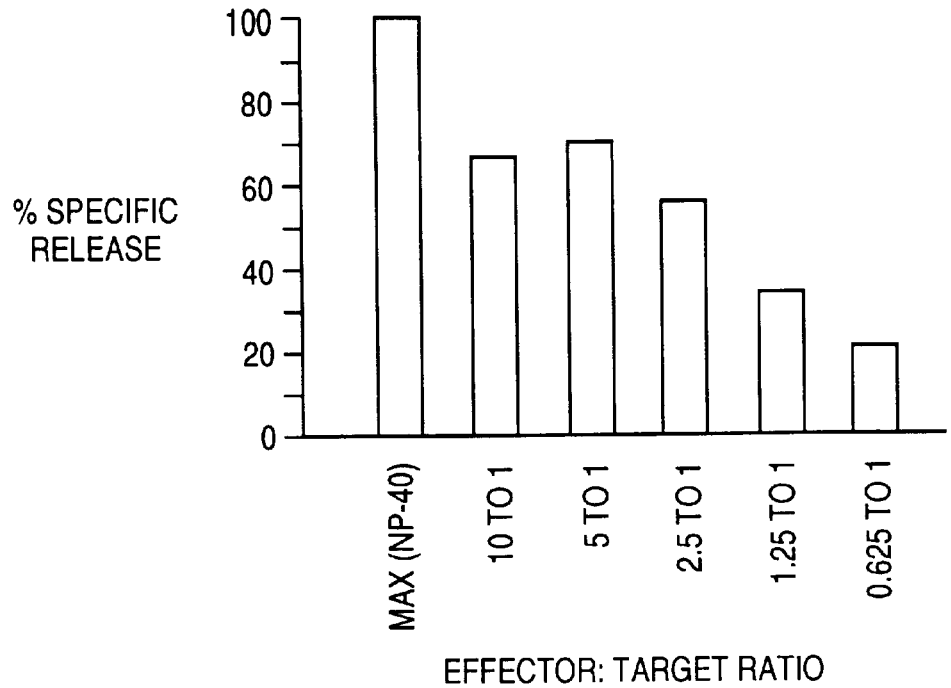
FIG. 2 is a graph depicting lysis of Raji cells caused by different concentrations of the antibody of the present invention.
Figure 2B:
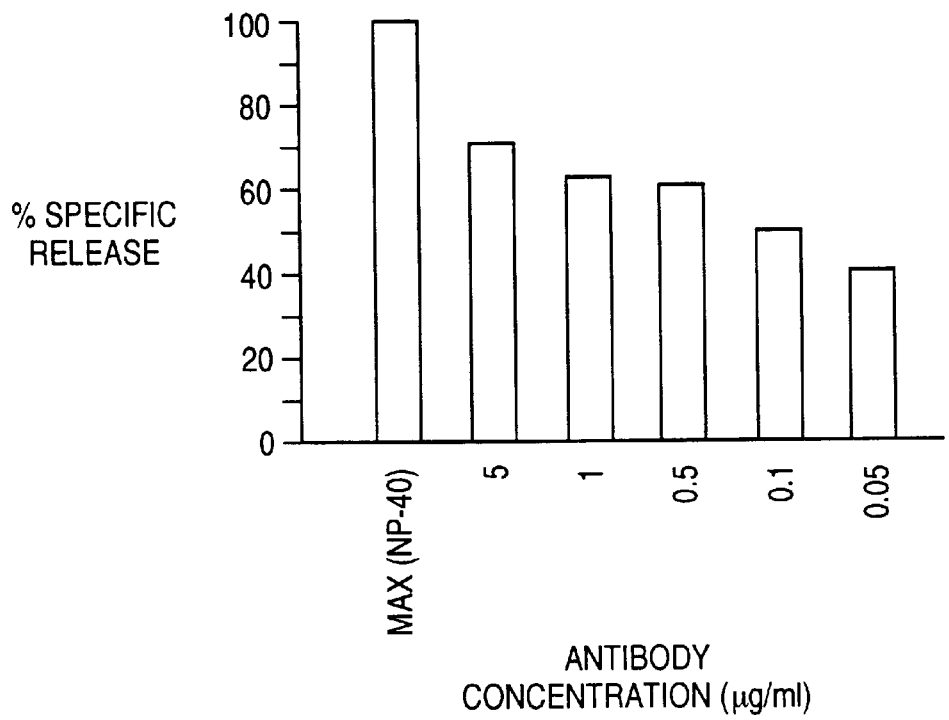

FIG. 2 shows 1DT3-D can induce significant lysis of raji cells at low T cell: Raji cell ratios (less than 1:1) and at low antibody concentrations (less than 0.1 ug/ml. Similar results were seen with other target cell lines.

Figure 3:
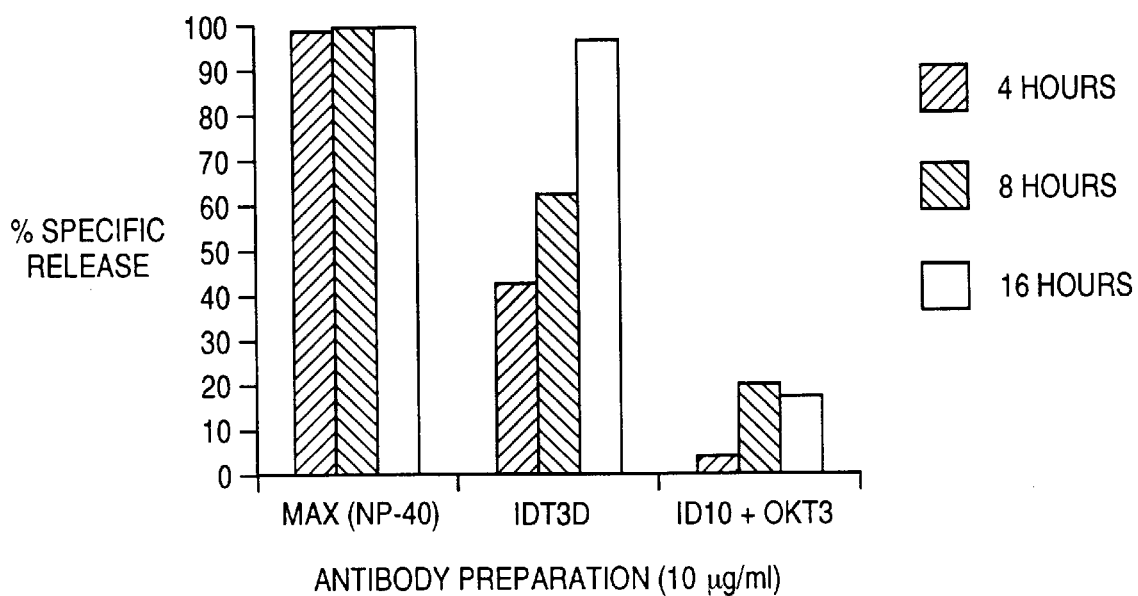
FIG. 3 is a graph depicting lysis of KH cells over a period of time by the bispecific antibody of the present invention also depicting a comparative study.

FIG. 3 shows 1DT3-D-induced T-cell-mediated lysis of fresh KH cells was noted after long incubation times.

The bispecific antibody of the present invention can also be produced simply by taking the Fab or F(ab')$_2$ fragments of the 1D10 antibody fusing these with portions of the OKT3 antibody to form a bispecific antibody of the present invention. Alternatively, bispecific antibodies, recognizing 1D10 and an antigen on natural killer cells or T cells, can be produced, by synthetic or genetic engineering techniques.

A benefit of the claimed bispecific antibodies is their ability to recognize malignant B-cells and distinguish these from non-malignant B-cells. Thus, therapy using the bispecific antibodies of the present invention is significantly less damaging than therapy using, for example, a non-specific antibody such as anti-CD19 antibody B4.

Further, as shown by the data described in the example, the antibody of the present invention induces significant lysis of malignant B-cells at relatively low T cell ratios. FIG. 2 shows that malignant to T cell ratios of less than 1:1 with relatively low antibody concentrations of less than 0.1 micrograms per ml provides significant destruction of the malignant cells. This is particularly important since it reduces the dependency on the concentration of T cells available in the patient. Further, it also reduces the amount of antibody required, thereby limiting any potential side effects.

EXAMPLE 2

In Vivo Efficacy of 1DT3-D Bispecific Antibody

This example describes an in vivo trial of the bispecific antibody 1DT3-D. Normal donor human peripheral blood lymphocytes were activated in vitro in the presence of OKT3 (2 µg/ml), and recombinant IL-2 (300 µg/ml). CB-17 scid/scid mice (Itoh et al., Cancer 72, 2686–2694 (1993)) were injected subcutaneously with $5 \times 10^6$ Raji cells mixed with $5 \times 10^6$ activated lymphocytes. 24-hr later, mice were injected with bispecific antibody, a monospecific antibody component of the bispecific antibody or no antibody. Mice were examined daily for the development of tumors of at least 0.5 cm at the site of tumor injection. Mice remaining tumor-free after 60 days were scored as negative and mice developing tumors within 60 days as positive. Control untreated mice always developed tumors within 21–28 days.

In a first experiment, 5 mice were treated with 10 µg/mouse of bispecific antibody 24 hours after inoculation with the mixture of malignant cells and activated human T-cells. A control group of 5 mice was inoculated with vehicle only. The tumor occurrence (i.e., development of a tumor of at least 0.5 cm within at least eight weeks) in the treated and control groups was as follows:

| Group | No tumors | Tumors | Total |
| --- | --- | --- | --- |
| Treatment | 4 | 1 | 5 |
| Control | 0 | 5 | 5 |

Using the Fischer's one-sided exact test, bispecific antibody treatment prolonged disease-free survival with a p value of 0.024.

A second experiment was designed to compare the anti-tumor effects of bispecific antibody with monospecific anti-CD3 and monospecific 1D10 at a dose of 10 µg/mouse in mice inoculated with tumor and T-cells as outlined above. Group 2 mice received monospecific 1D10 and monospecific OKT3, Group 3 received bispecific antibody and the control group received vehicle only. Group 4 mice also received bispecific antibody at a concentration of 10 µg/mouse, but these mice had previously been inoculated with unactivated T-cells as distinct from all other groups which received activated T-cells.

| Group | No tumors | Tumors | Total |
| --- | --- | --- | --- |
| Control | 0 | 5 | 5 |
| 2 | 5 | 0 | 5 |
| 3 | 5 | 0 | 5 |
| 4 | 2 | 3 | 5 |

Fisher's exact test for general two-way tables (Agresti, *Categorical Data Analysis* (Wiley, N.Y., 1990), pp. 64–65) was used to test the null hypothesis that the occurrence rates in the four groups are equal. There is a highly significant difference among the groups (p=0.001). Pairwise exact tests comparing the control group to each of groups 2, 3, and 4 were also carried out. The corresponding one-sides p-values are 0.004, 0.004, and 0.222. Thus, groups 2 and 3 are both significantly different from the control group. It was concluded that at a dose of 10 µg/mouse treatment with bispecific antibody or a combination of both component monospecific antibodies prolonged tumor-free survival.

In a third experiment, a dose-response study was performed to test the anti-tumor effects of varying dosages of bispecific antibody. Separate groups of mice were respectively treated with dosages of 0.4, 2 or 10 µg/mouse bispecific antibody or vehicle.

| Group | No tumors | Tumors | Total |
| --- | --- | --- | --- |
| Control | 0 | 5 | 5 |
| 0.4 | 1 | 4 | 5 |
| 2 | 5 | 0 | 5 |
| 10 | 4 | 1 | 5 |

The Cochran-Armitage trend test, (Agresti, *Categorical Data Analysis* (Wiley, N.Y., 1990), pp. 100–102, 118–119) was used to test the null hypothesis that the occurrence rates in the four groups are equal, versus the alternative hypotheses of a linear trend. Using equally-spaced scores, the p-value is 0.001; using the scores 0, 0.4, 2, and 10, the p-value is 0.0164. Both sets of scores indicate a significant trend in the proportions. These results show that the bispecific antibody is effective to prolong survival time and that mice receiving larger doses (10 µg and 2 µg) have improved tumor-free survival.

A fourth experiment was designed to compare monospecific OKT3 and 1D10 to bispecific antibody at a dose of 2 µg antibody/mouse.

| Group | No tumors | Tumors | Total |
| --- | --- | --- | --- |
| Control | 0 | 5 | 5 |
| 2 | 0 | 5 | 5 |
| 3 | 1 | 4 | 5 |
| 4 | 4 | 1 | 5 |

Tumor-free survival of mice treated with monospecific OKT3 (Group 2) and monospecific 1D10 (Group 3) was not significantly different from control, whereas mice treated with bispecific antibody (Group 4) had prolonged survival using the Fisher's exact test for general two-way tables.

These data indicate that systemic administration of 1DT3-D kills and/or prevents the development of malignant B-cells in vivo and that a dose of 2 µg/animal, bispecific antibody therapy is more effective than monospecific antibody therapy.

EXAMPLE 3

Generation of a Monoclonal Antibody Against the Human CD3 Antigen

The 1DT3-D antibody described in Example 1 incorporated OKT3 as the binding moiety having an affinity for effector cells. The present example describes the isolation of an alternative antibody, M291, for use as the effector-cell binding component in a bispecific antibody.

Human peripheral blood mononuclear cells (PBMC) were activated with PHA and IL-2 to expand T cells. Activated T cells were used as immunogens in Balb/C mice. Hybridomas were generated from the spleens of these mice by standard methods. These hybridomas were screened for antibodies that could stimulate PBMC to proliferate in vitro. Anti-CD3 antibodies with the appropriate Fc cause T cells in PBMC to proliferate. One of these hybridomas, M291, was isolated and found to secrete an antibody of the isotype IgG2a/kappa that could activate T cells to proliferate. The purified antibody M291 competes with another anti-human CD3 antibody, OKT3, (IgG2a/kappa) for binding to human T cells, showing that the epitopes recognized by the respective antibodies are closely spaced. M291 is thus an antibody having the specificity against the human CD3 complex.

EXAMPLE 4

Humanization of 1D10 and M291 Antibodies

This example describes the separate humanization procedures for the 1D10 and M291 antibodies.

(1) Cloning of 1D10 and M291 V region cDNAs

Heavy and light V domain cDNAs for 1D10 and M291 were cloned using an anchored PCR method (see Loh et al., *Science* 243, 217 (1989)). cDNAs were first synthesized by reverse transcriptase after priming polyA+ RNAs from the hybridoma cells with oligo dT. A tail of dGs was added to the 3' terminus of the cDNA by terminal deoxynucleotidyl transferase. The V domains were then amplified by PCR with 3' primers that hybridized to the C regions and 5' primers that hybridized to the G-tails. Several independent H and L chain clones were sequenced to ensure no sequence mistakes were introduced by PCR. For 1D10, the V domains were expressed as an antibody of the mouse isotype IgG2a/kappa by transfecting the genes in suitable vectors into the myeloma cell line SP2/0 to confirm they coded for the binding site of 1D10. The expression vectors used in the transfection are similar to the plasmids pVk.G and pVg.D described by Co et al. (see Co et al., *J. Immunol.* 148, 1149 (1992)), except that genes for the constant regions were derived from mouse sequences. Antibody isolated from the transfected cells was found by flow cytometry to bind to Raji cells in a pattern indistinguishable from that of the parent mouse IgG1/kappa 1D10 antibody. The V domains of M291 were cloned similarly and they were expressed as mouse F(ab'-zipper)$_2$ (see Kostelny et al., *J. Immunol.* 148, 1547 (1992)). Flow cytometry assay indicated M291-Fos F(ab'zipper)$_2$ binds to human T cells with similar or identical affinity as the parent antibody. This observation confirmed that the correct V domains of M291 were cloned.

(2) Modelling and design of humanized sequences

The sequences of human V domains most similar to murine 1D10 and M291 were selected to serve as the framework of the humanized antibody. For 1D10, the best human $V_k$ sequence was R3.5H5G of human subgroup I with only sixteen differences from 1D10 in framework regions. Manheimer-Lory et al., *J. Exp. Med.* 174, 1639–1652 (1991). The best $V_H$ sequence was IC4 of Kabat's subgroup II or subgroup IV (see Id.), with twenty-six differences. For M291, the best human $V_k$ sequence is HF2-1/17 of human subgroup I with twenty-six amino acid differences from M291 in framework regions (Athison et al., *J. Clin. Invest.* 75, 1138 (1985); Lampman *Blood* 74, 262 (1989)); the best human $V_H$ sequence is 21/28 of human subgroup I with twenty amino acid differences. Dersimonian et al., *J. Immunol.* 139, 2496–2501 (1987). With the help of the 3-dimensional model, an additional number of framework positions that differed between the murine antibodies and the chosen human sequences were identified. The location of those amino acid residues in 3-dimensional space relative to the hypervariable regions, or CDRs, indicated they were likely to influence CDR conformation, and thus binding affinity. Murine sequences were used in these positions. A number of positions were identified in the human sequences that differed from the consensus of their respective subgroups. These amino acids were changed to correspond to consensus sequences. $V_H$ and $V_L$ sequence comparisons between the murine and humanized 1D10, and between the murine and humanized M291, are shown in FIG. 4 and FIG. 5, respectively.

(3) Synthesis and expression of humanized 1D10 antibody

DNA segments encoding the humanized 1D10 L and H chain V regions were constructed by total gene synthesis from overlapping oligonucleotides. These mini exons included signal sequences, J segments and splice donor sequences and were surrounded by XbaI sites. The DNA segments were incorporated in an expression vector using the scheme outlined in FIG. 6.

The humanized V domains were cloned into the XbaI sites of the corresponding heavy and light chain expression plasmids pV$_g$1.D.Tt and pVk.rG.dE. The resulting plasmids are called pHu1D10.Vg1.D.Tt and pHu1D10.V$_k$.rG.dE. The heavy chain expression vector, pVg1.D.Tt, which contains the mutant dihydrofolate reductase gene (mdhfr) as the selectable marker (see Simonsen & Levinson, *Proc. Natl. Acad. Sci. USA,* 80, 2495, (1983)), the human cytomegalovirus (hCMV) major immediate early promoter and enhancer for transcription initiation (see Boshart et al., *Cell* 41, 521 (1985)), and the human IgG1 constant regions was constructed from the respective fragments by standard methods. It differs from the vector pV$_g$1.D described by Co et al, *J. Immunol.* 148, 1149 (1992) by having a transcription termination site 3' to the γ 1 gene poly(A) site. The transcription termination site (Tt) was derived from the sequence located downstream from the human complement gene C2 (+37 to +162 bp from the C2 poly(A) site) (see Ashfield et al., *EMBO J.* 10, 4197 (1991)) and was synthesized entirely by using overlapping oligonucleotides.

For light chain expression, a vector was constructed from the hCMV promoter and enhancer, the human C$_K$ gene including part of the preceding intron, and the xanthine-guanine phosphoribosyltransferase (gpt) gene (see Mulligan & Berg, *Proc. Natl. Acad. Sci. USA,* 78, 2072 (1981)) for selection. The vector, pV$_k$.rG.dE, is similar to pV$_k$ described by Co et al. (see Co et al., *J. Immunol.* 148, 1149 (1992)) except for the orientation of the gpt gene. In addition, one of the two repeated sequences in the enhancer region of the SV40 promoter used to transcribe the gpt gene was deleted by SphI digestion.

For coexpression of heavy and light chains in one plasmid, an EcoRI fragment containing the hCMV promoter, the $V_H$ exon, the $C_H1$, $C_H2$ and $C_H3$ exons, the polyA signal, and the transcription termination signal was taken from the heavy chain expression vector and cloned into the unique EcoRI site of the corresponding light chain expression plasmid. Due to the presence of the transcription termination signal situated between them, the two genes are transcribed independently by the hCMV promoter. After transcription the humanized $V_H$ exon is spliced to the human γ 1 $C_H1$, hinge, $C_H2$ and $C_H3$ exons, and then polyadenylated. Similarly the $V_L$ exon is spliced to the human $C_K$ exon. The predicted amino acid sequences of the mature light and heavy chains of humanized 1D10 are shown in FIGS. 4C and 4E, respectively.

Plasmid pHu1D10.IgG1.rG.dE, was used for transfection into mouse myeloma cell line TSO by electroporation. TSO cells are derivative of mouse myeloma NSO cells (ECACC 85110503) selected for their ability to grow in serum-free media according to the procedure of Sato et al., *J. Exp. Med.* 165, 1761 (1987). The cells from each transfection were selected for gpt expression. Because the SV40 promoter/enhancer for the gpt gene has been crippled, only few transfectants can express gpt high enough to survive the selection (see Jasin & Berg, *Genes Dev.* 2, 1353 (1988)). Transfection efficiency is about $0.5–1.0\times10^{-6}$; compared to the efficiency of $10–50\times10^{-6}$ from transfection using near identical plasmid containing the wild type SV40 promoter for gpt. When screened for production of humanized antibodies by standard ELISA, the average surviving cells also gave higher levels of antibody compared to those transfected with plasmid containing the wild type SV40 promoter. The best antibody producer was then subcloned for the production of the humanized 1D10. The antibody, Hu1D10, was purified from the serum-free spent medium by Protein A affinity chromatography.

(4) Properties of Hu1D10

Figure 7A:
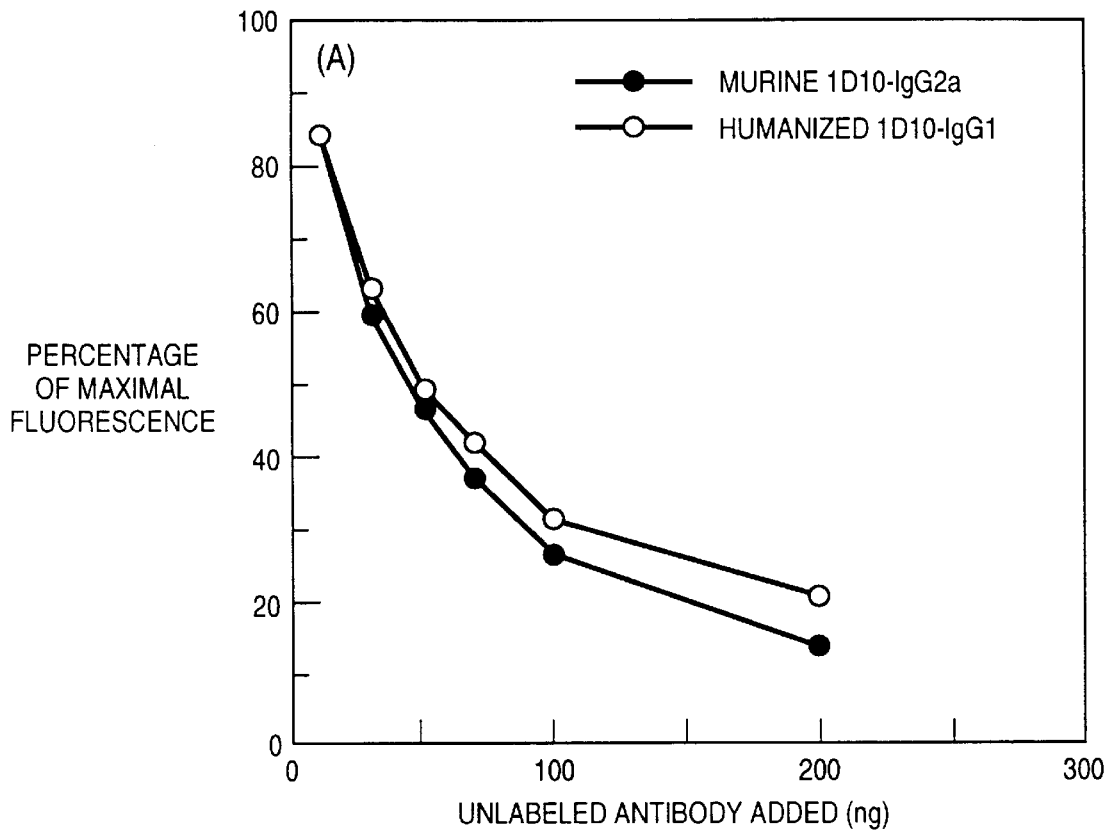
FIG. 7. (A). Displacement assay to compare the relative affinity of humanized 1D10 and murine 1D10 for the antigen. Subsaturation amounts of murine 1D10-IgG2a-FITC on Raji cells were displaced by increasing amounts of murine 1D10-IgG2a or humanized 1D10-IgG1. Raji cells were resuspended in complete media at 2.5×10$^6$/ml. Dilutions of the test (humanized 1D10-IgG1) or control (murine 1D10-IgG2a) antibody were added and incubated at 4° C. for 1 hour. A fixed, subsaturation amount of murine 1D10-IgG2a-FITC was added, and the cells were incubated at 4° C. for 1 hour, washed, and resuspended in 1% paraformaldehyde. The cells were then analyzed using flow cytometry. Values expressed in % inhibition of fluorescence intensity compared to no competitive antibody control. (B). Scatchard plot analysis of the binding of $^{125}$I-labeled humanized 1D10-IgG1 to Raji cells. Scatchard analysis was made by making dilutions of labeled antibody to 4×10$^5$ Raji cells in 0.2 ml for 90 min at 0° C. The cells were washed in binding buffer (2% horse serum in PBS containing 0.1% sodium azide) and counted. Nonspecific binding was determined by inhibiting the specific binding with an excess of nonlabeled humanized 1D10-IgG1. The apparent Ka and the number of binding sites were calculated from the slope and the X axis intercept, respectively, of the Scatchard plot.
Figure 7B:
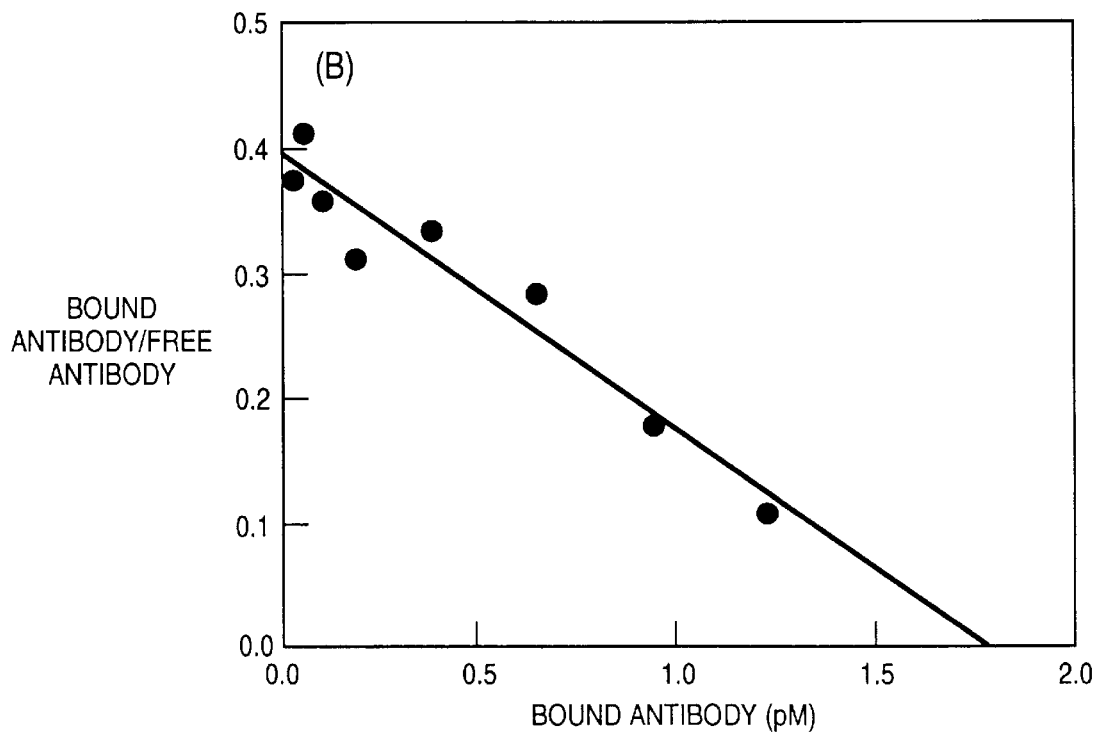
Figure 8A:
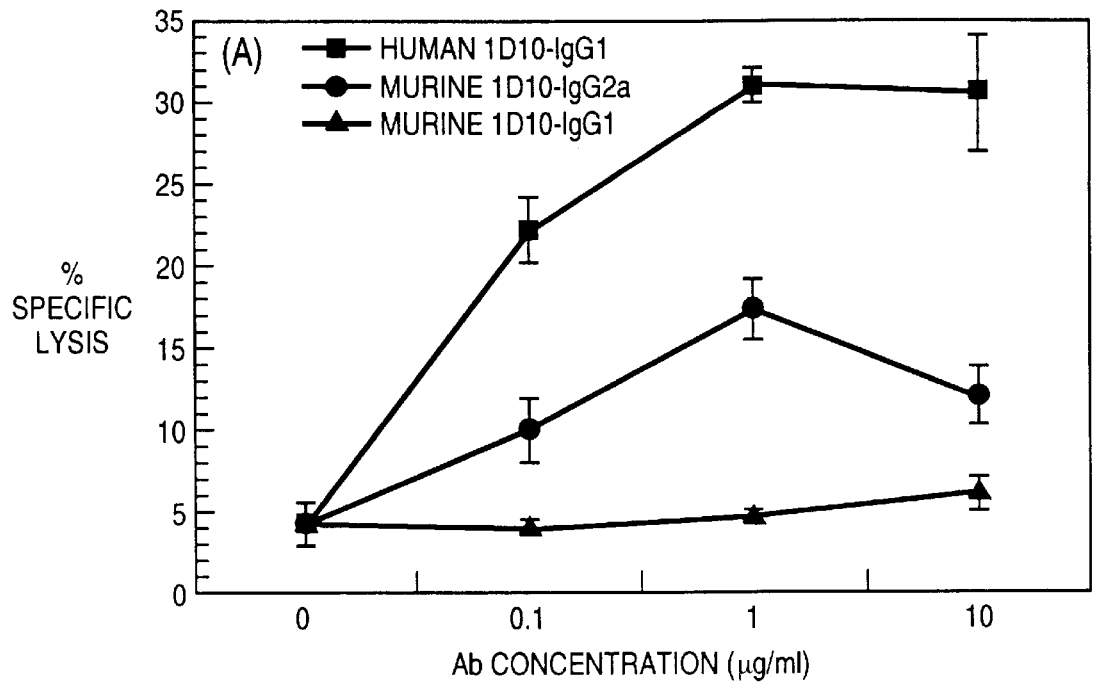
FIG. 8. (A). Antibody-dependent cell-mediated cytotoxicity (ADCC) capability by various 1D10 isotypes. $^{51}$Cr-labeled Raji human lymphoma cells were used as targets for (▲) murine 1D10-IgG1, (●) murine 1D10-IgG2a, or (■) humanized 1D10-IgG1 and human peripheral mononuclear as effector cells. The effector:target ratio was 40:1. Spontaneous release was less than 20% of total release. Bars represent SEM. (B). Complement-mediated cytotoxicity by various 1D10 isotypes. $^{51}$Cr-labeled Raji human lymphoma cells were used as targets for (▲) murine 1D10-IgG1, (●) murine 1D10-IgG2a, or (■) humanized 1D10-IgG1 and human sera from a normal subject as complement. Spontaneous release was less than 20% of total release. Bars represent SEM.
Figure 8B:
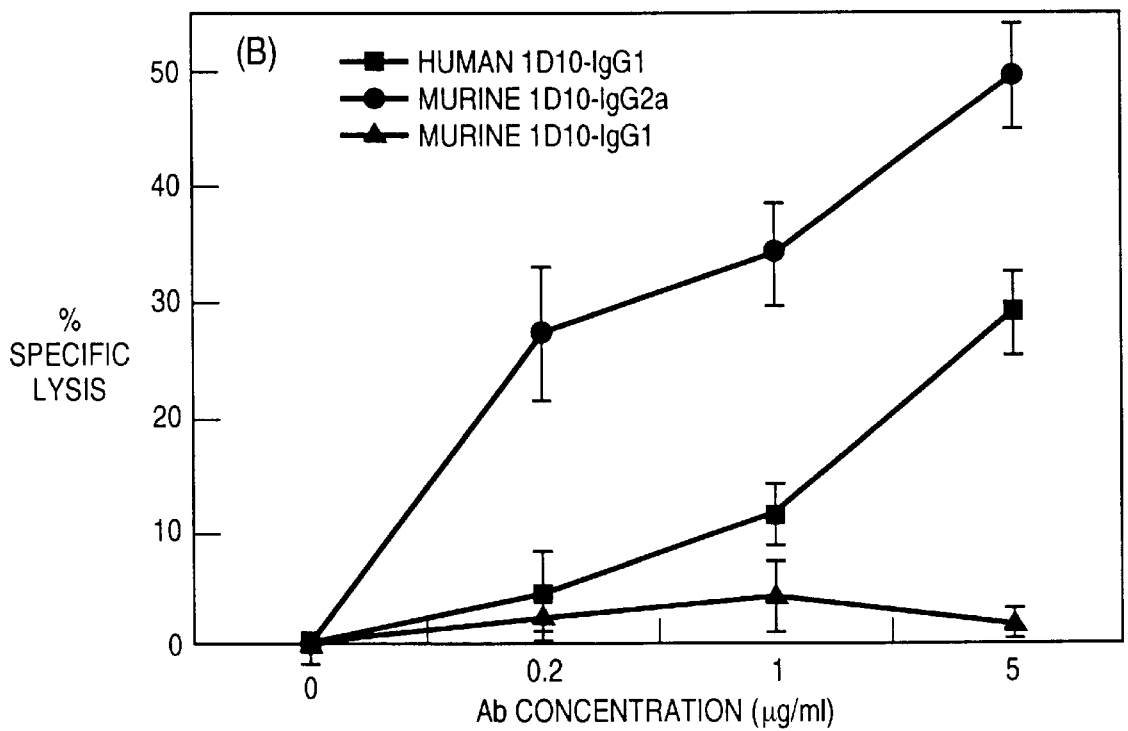

Murine 1D10-IgG2a and humanized 1D10 had identical spectrums of reactivity with 1D10 positive and 1D10 negative cell lines. The affinity of murine 1D10-IgGa and humanized 1D10 for cells bearing the target antigen was evaluated using a displacement assay (see Woodle et al., *J. Immunol.* 148 2756 (1992)). In this assay, the ability of prebound humanized 1D10 or murine 1D10-IgG2a to inhibit the binding of FITC-labeled murine 1D10-IgG2a was quantitated by FACS analysis. Humanized 1D10 competitively inhibited the binding of murine 1D10-IgG2a to a degree similar to that seen with the parent antibody (FIG. 7A). These data indicated that the humanized antibody binds with similar affinity as the murine antibody. Scatchard analysis was used to better estimate the apparent affinity of humanized 1D10. Humanized 1D10-IgG1 was found to have an apparent $K_a$ of $2.3\times10^8M^{-1}$, and there are about $5\times10^5$ sites per cell in the Raji cell line (FIG. 7B). In addition, humanized 1D10 has the ability to direct ADCC and complement mediated lysis, two effector functions that are not present in the original murine 1D10 (FIGS. 8A and 8B).

(5) Synthesis and expression of humanized M291 and 1D10(ab'-zipper)$_2$

Figure 6:
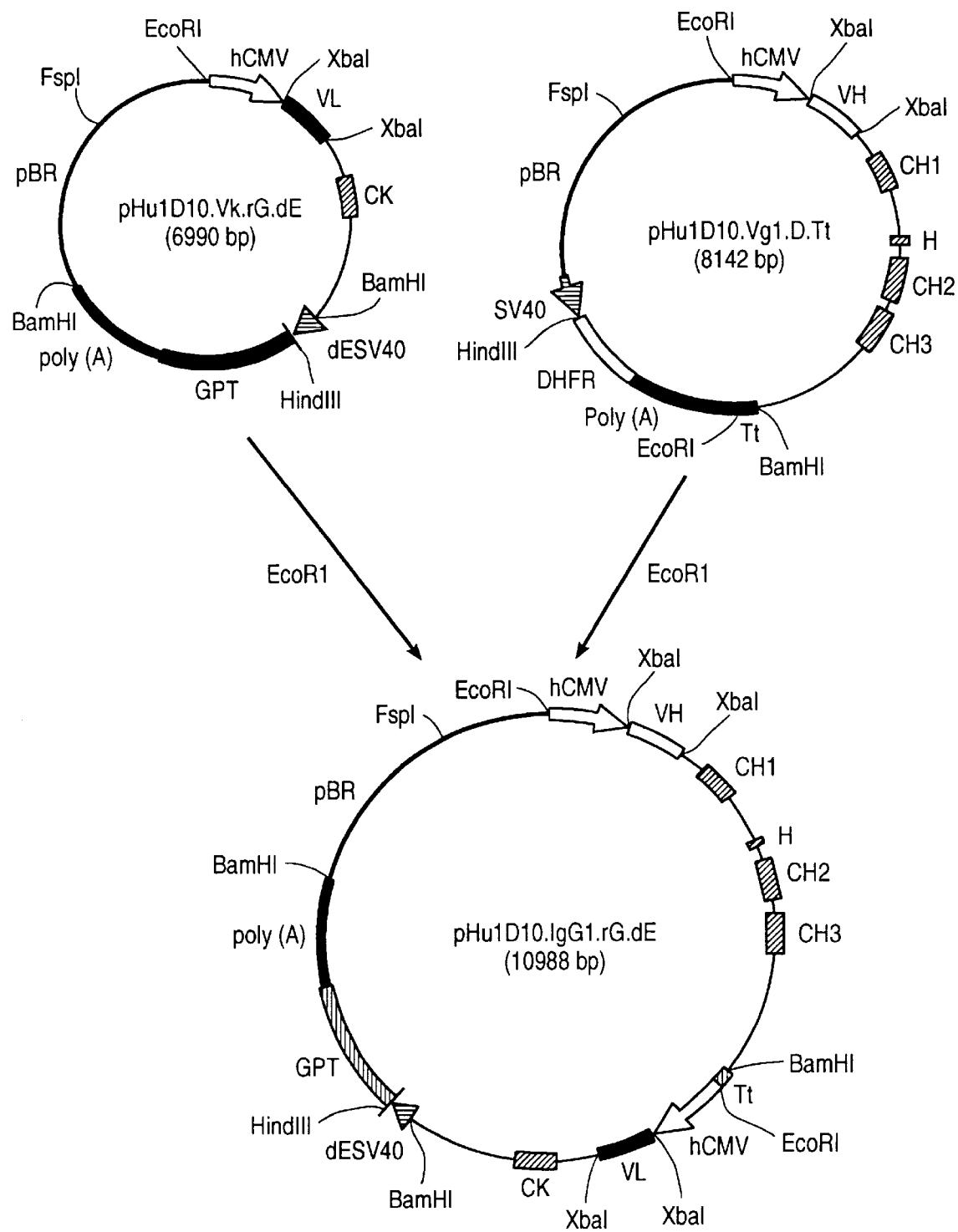
FIG. 6. Construction of the plasmid pHu1D10.IgG1.rG.dE used for the expression of the humanized 1D10 IgG1.
Figure 9A:
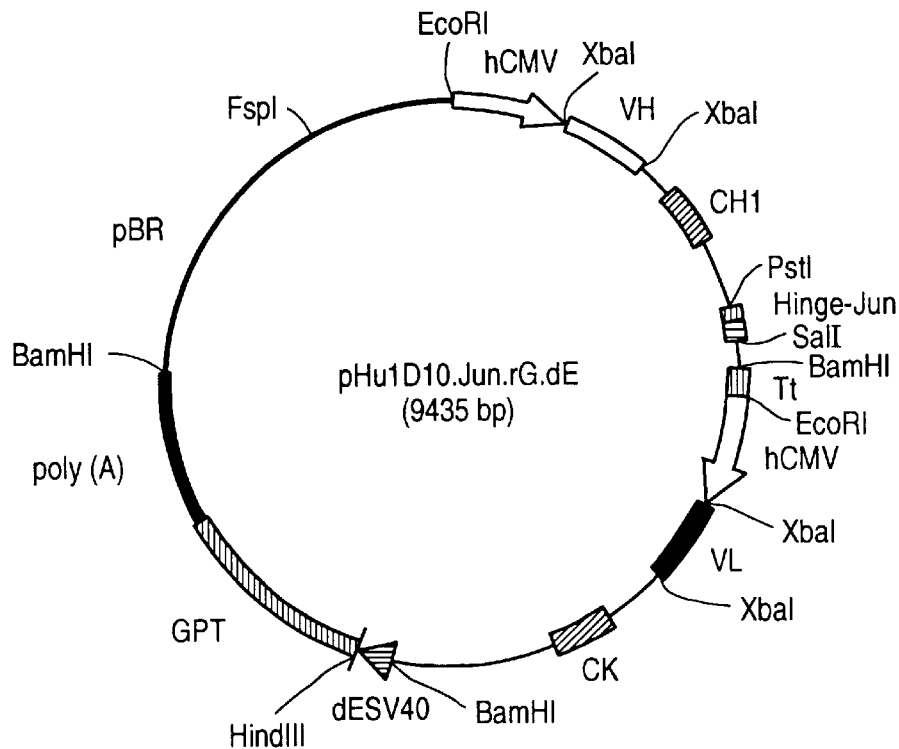
FIG. 9. Schematic diagrams of the plasmids pHu1D10-Jun.rG.dE and pHuM291-Fos.rG.dE for the expression of Hu1D10-Jun and HuM291-Fos F(ab'-zipper)$_2$. The constructions of these two plasmids were similar to that of pHu1D10.IgG1 in FIG. 6 except for the replacement of the $C_H2$ and $C_H3$ exons by the leucine zipper sequences Jun and Fos. The polyadenylation signal for the Fd-zipper transcript is from the 3' noncoding sequence of mouse IgG2a gene (see Kostelny et al., *J. Immunol.* 148, 1547 (1992)).
Figure 9B:
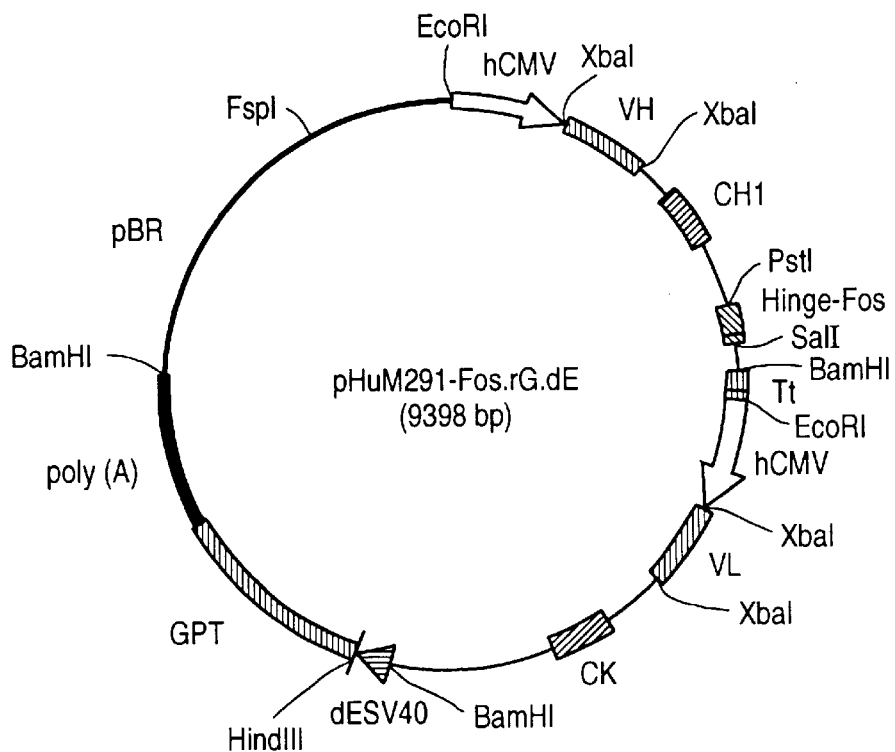

Leucine zipper genes, Jun and Fos, were synthesized as described by Kostelny et al., *J. Immunol.* 148, 1547 (1992). The resulting PCR products were 179 bp PstI-SalI fragments, encompassing the entire hinge zipper gene fusion. The PstI site is the natural restriction site located at the beginning of the hinge exon, but the SalI site was added to the end of the zipper sequences during PCR. The hinge/zipper exon was inserted with a 162 bp SalI-BamHI fragment containing the 3' noncoding sequence of the mouse IgG2a gene into the heavy chain expression vector pVg1.D.Tt, replacing the hinge, $C_H2$ and $C_H3$ exons in the plasmid. Coexpression of the truncated heavy chain (Fd) gene with light chain gene in one plasmid is essentially the same as described above for pHu1D10.IgG1.rG.dE (FIG. 6). The expression plasmids are called pHu1D10-Jun.rG.dE and pHuM291-Fos.rG.dE (FIG. 9). The differences between these plasmids and those used to express the whole antibody are: (1) the human γ1 $C_H1$ exon is now spliced to the hinge/zipper fusion exon instead of the hinge, $C_H2$ and $C_H3$ exons, and (2) the transcript is polyadenylated by a heterologous signal. The leucine zipper Jun is used for the Fd of Hu1D10, and Fos for Fd of HuM291. When combined with the corresponding light chain, the Fd-zipper would form F(ab'-zipper)$_2$. The humanized F(ab'-zipper)$_2$ fragments for 1D10 and M291 are called Hu1D10-Jun and HuM291-Fos, respectively. The predicted amino acid sequences of the heavy chain Fd-zipper in Hu1D10-Jun and HuM291-Fos are shown in FIGS. 4D and 5D, respectively. In both cases there were modifications of the human IgG1 hinge at the region of hinge/zipper fusion (FIG. 10). An insertion of two amino acid residues Lys-Cys derived from the mouse IgG2a hinge was introduced to the hinge exon to provide an additional inter-heavy chain disulfide bond. The insertion of these two residues in the human IgG1 hinge renders its COOH-terminal half homologous to that of the mouse IgG2a hinge. The modified hinge would have three inter-heavy chain disulfide bonds compared to two in the wild type human IgG1. In addition an Ala residue (first residue of the $C_H2$ domain) and two Gly residues were introduced at the fusion junction to make the joints more flexible. The expression plasmids, pHu1D10-Jun.rG.dE and pHuM291-Fos.rG.dE, were separately transfected into mouse myeloma cell line TSO by electroporation. Transfectants were screened for the presence and the quantity of secreted F(ab'-zipper)$_2$ fragments by ELISA. F(ab'-zipper)$_2$ fragments were purified using Protein G affinity chromatography.

(5) Properties of HuM291-Fos

Figure 11A:
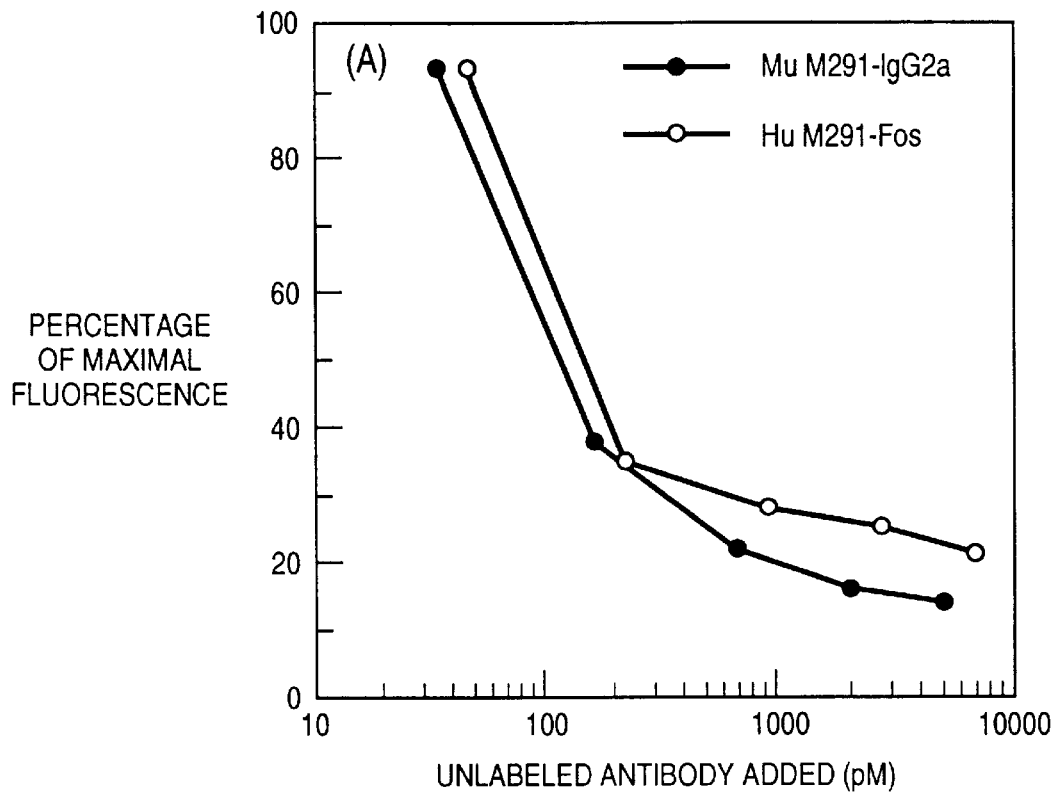
FIG. 11. (A). Displacement assay to compare the relative affinity of HuM291-Fos and M291 for their antigen. Subsaturation amounts of murine M291-FITC on human T cells were displaced by increasing amounts of murine M291 or HuM291-Fos. T cells were resuspended in complete media at $2.5\times10^6$/ml. Dilutions of the test (HuM291-Fos) or control (murine M291) antibody were added and incubated at 4° C. for 1 hour. A fixed, subsaturation amount of murine M291-FITC was added, and the cells were incubated at 4° C. for 1 hour, washed, and resuspended in 1% paraformaldehyde. The cells were then analyzed using flow cytometry. Values expressed in % inhibition of fluorescence intensity compared to no competitive antibody control. (B). Scatchard plot analysis of the binding of $^{125}$I-labeled HuM291-Fos to activated human T cells. Scatchard analysis was made by binding dilutions of labeled antibody to $4\times10^5$ T cells in 0.2 ml for 90 min at 0° C. The cells were washed in binding buffer (2% horse serum in PBS containing 0.1% sodium azide) and counted. Nonspecific binding was determined by inhibiting the specific binding with an excess of nonlabeled HuM291-Fos. The apparent $K_a$ and the number of binding sites were calculated from the slope and the X axis intercept, respectively, of the Scatchard plot.
Figure 11B:
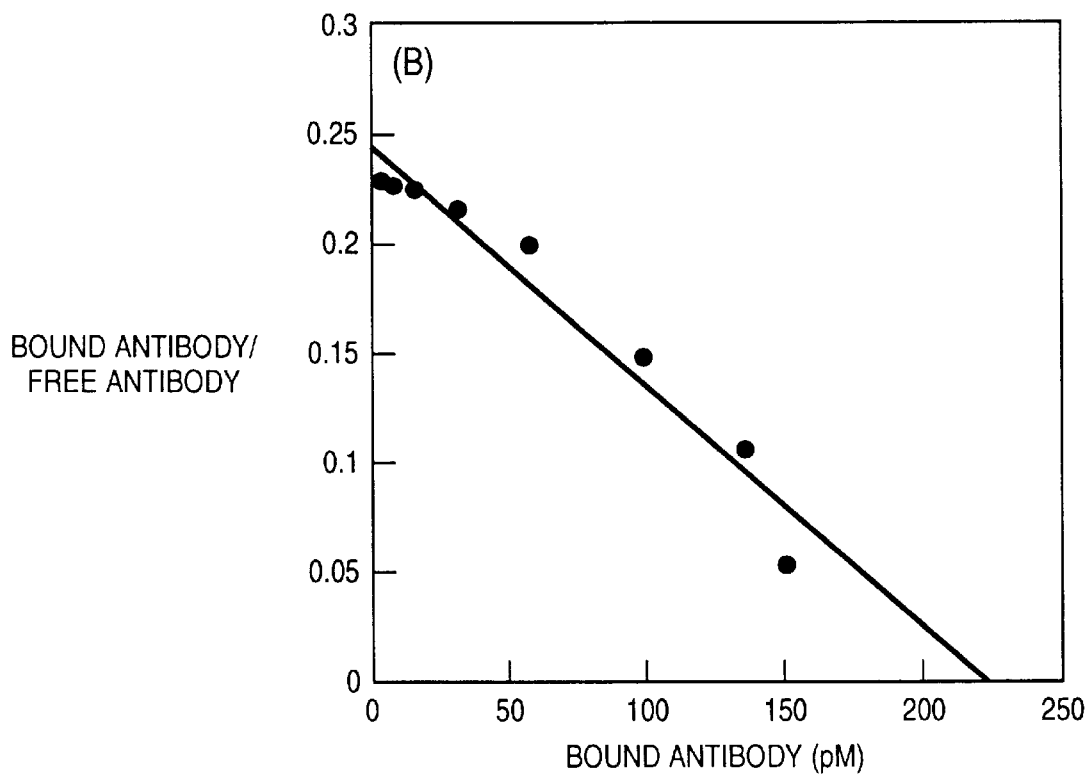

The relative affinity of murine M291 and HuM291-Fos F(ab'-zipper)$_2$ for T cells was evaluated using the displacement assay described above. HuM291-Fos blocks the binding of FITC-labeled murine M291 IgG2a as well as the unlabeled M291 (FIG. 11A). The affinity of HuM291 for CD3 is estimated to be within 2–3 fold of M291's. Scatchard analysis indicated the apparent affinity of HuM291-Fos was $K_a \sim 1.1\times10^9M^{-1}$, and there are about $6.6\times10^4$ sites per cell in activated human T cells (FIG. 11B).

(6) Formation of the bispecific Hu1D10-Jun×HuM291-Fos F(ab'-zipper)$_2$ in vitro Hu1D10-Jun and HuM291-Fos were mixed in equal molar at concentrations between 0.5 to 3.0 mg/ml and reduced with 10 mM DTT in PBS at 37° C. for 1 hour to form Fab'-zippers. They were passed through Sepharose G-50 column in PBS to remove DTT. The desalted protein was incubated at 4° C. for 48 hours to allow formation of heterodimeric bispecific Hu1D10-Jun ×HuM291-Fos. The bispecific molecules were further purified by hydrophobic interaction chromatography (HIC) on a Phenyl Sepharose column.

EXAMPLE 5

T Cell-mediated Cytotoxicity by Humanized Bispecific Antibodies

Figure 12:
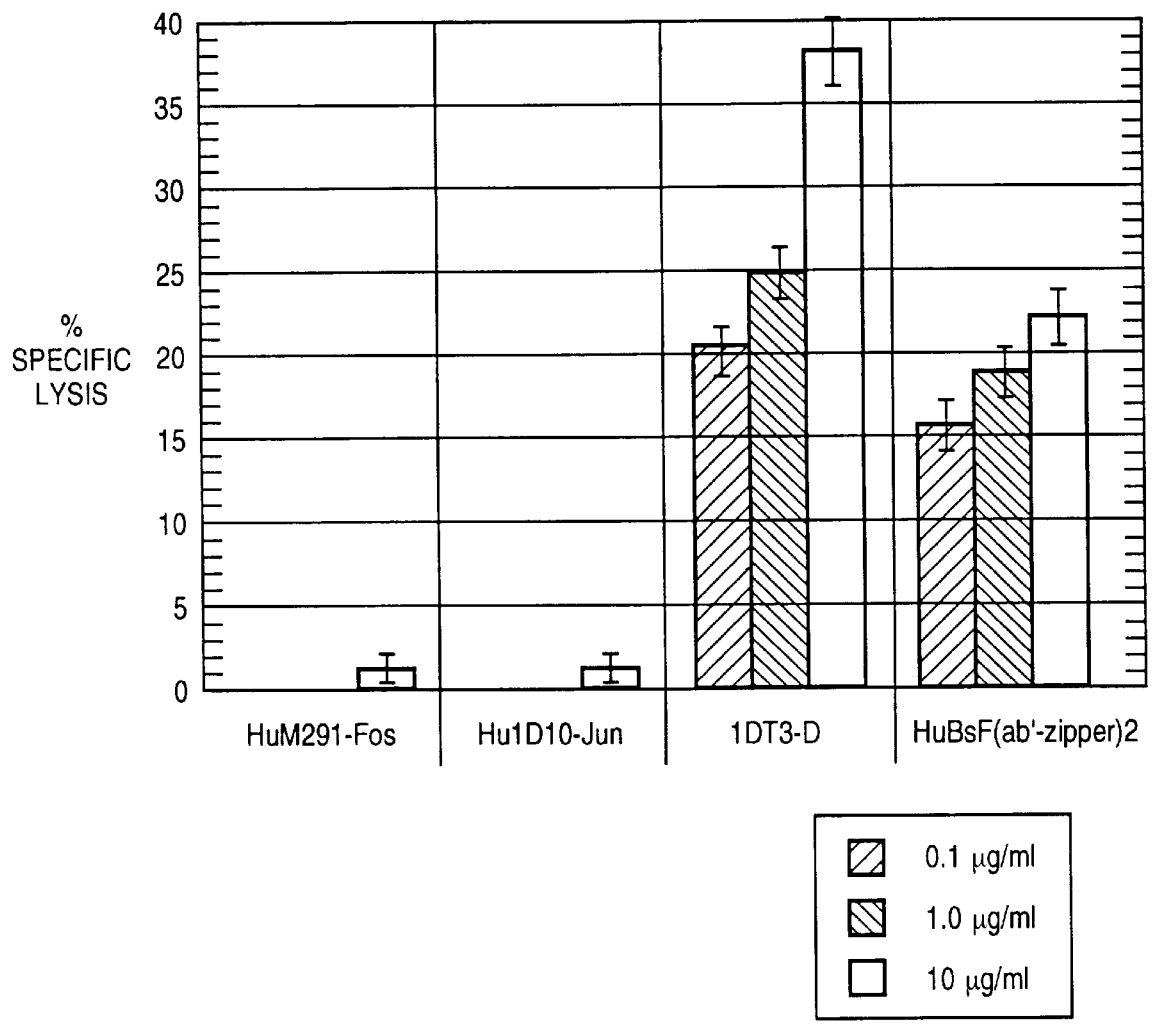
FIG. 12. Bispecific antibody induced T cell mediated lysis of 1D10 positive cells. T cells in human PBL were activated by anti-CD3 antibody OKT3 and expanded by culturing them in IL-2. Target cells were labeled with $^{51}$Cr and washed. T cells and labeled target cells at effector: target ratio of 25:1 were plated in V bottom microtiter plates. Antibodies at desired concentration were added. Antibodies used were: Hu1D10-Jun, HuM291-Fos, the mouse bispecific IgG 1DT3-D, and the humanized bispecific F(ab'-zipper)$_2$ Hu1D10-Jun×HuM291-Fos. Plates were incubated at 37° C. for 4 hours, centrifuged, and target cell lysis was measured by determining the amount of $^{51}$Cr released. Percentages of specific release in this cytotoxicity assay were calculated as: {Counts released by antibody minus counts released without added antibody}/{Counts released by 0.1% SDS minus counts released without added antibody}×100.

The ability of Hu1D10-Jun×HuM291-Fos to direct T cell-mediated lysis was tested in a chromium-release assay. Human T cells derived from PBMC after OKT3 and IL-2 treatment were used as effector cells. Dawo, which is a cell line developed from a patient with large B cell lymphoma, was used as target cells. FIG. 12 shows that the bispecific Hu1D10-Jun×HuM291-Fos, as well as the mouse bispecific IgG 1DT3-D directed T cells to lyse target cells. The two bispecific molecules seemed to have similar activities at low antibody concentrations. The two parent antibodies, HuM291-Fos and Hu1D10-Jun, were not effective in this assay, either singly or in combination.

At high concentrations (10 μg/ml, 1DT3-D had higher activity than Hu1D10-Jun×HuM291-Fos in mediating target cell lysis. This was because of low affinity Fc receptors on the surface of the target cells. At high antibody concentration, bispecific IgG's Fc could bind to these receptors and direct T cell to lyse target cells independent of the target antigen, a mechanism known as reverse lysis (see Weiner et al., J. Immunol. 152, 2385 (1994)). Because Hu1D10-Jun×HuM291-Fos is an F(ab')$_2$-like molecule without an Fc, it cannot initiate lysis by binding to an Fc receptor. In some therapeutic application, the property of the humanized antibody is advantageous in increasing selective toxicity of the antibody.

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A bispecific antibody that binds to:
   (a) a first antigen on the surface of effector cells selected from the group consisting of T-cells and natural killer cells, and
   (b) a second antigen on a 28/32 kDa heterodimeric protein on the surface of malignant B cells, which second antigen specifically binds to an antibody designated 1D10, having a light chain variable domain designated SEQ. ID. No. 2 and a heavy chain variable domain designated SEQ. ID. No. 4,
   wherein the binding of the bispecific antibody to the first and second antigens results in killing of the malignant B cells.

2. The bispecific antibody of claim 1, wherein the effector cells are T cells.

3. The bispecific antibody of claim 2, wherein the bispecific antibody binds to a CD3 antigen on the T cells.

4. The bispecific antibody of claim 3, wherein the bispecific antibody is produced by the cell line ATCC HB 1099.3.

5. A cell line producing the bispecific antibody of claim 1.

6. The cell line of claim 5 that is a hybrid-hybridoma formed from two hybridomas,
   a first hybridoma producing an antibody that binds to the first antigen, and
   a second hybridoma producing an antibody that binds to the second antigen.

7. The cell line of claim 6, wherein the effector cells are T-cells and the first hybridoma produces an antibody that binds to a CD3 antigen on the T-cells.

8. A cell line designated ATCC HB 10993.

9. An antibody designated 1D10, having a light chain variable domain designated SEQ. ID. No. 2 and a heavy chain variable domain designated SEQ. ID. No. 4.

10. A humanized version of the antibody of claim 9.

11. A humanized antibody according to claim 10, the antibody comprising a humanized heavy chain and a humanized light chain:
   (1) the humanized light chain comprising three complementarity determining regions, CDR1, CDR2 and CDR3, of the 1D10 immunoglobulin light chain, and a variable region framework from a human kappa light chain variable region framework sequence provided that at least one position selected from a first group consisting of L48, L49, L69, and L70 is occupied by the same amino acid present in the equivalent position of the 1D10 immunoglobulin light chain variable region framework; and
   (2) the humanized heavy chain comprising three complementarity determining regions, CDR1, CDR2 and CDR3, of 1D10 immunoglobulin heavy chain, and a variable region framework from a human heavy chain variable region framework sequence provided that at least one position selected from a second group consisting of H27, H29, H30, H37, H67, H71, H78 and H83 is occupied by the same amino acid present in the equivalent position of the mouse 1D10 immunoglobulin heavy chain variable region framework;
   wherein the humanized antibody specifically binds to a 28/32 kDa heterodimeric protein on the surface of malignant B cells with a binding affinity having a lower limit of about $10^7$ $M^{-1}$ and an upper limit of about five-times the binding affinity of the 1D10 immunoglobulin.

12. The humanized antibody of claim 11, wherein
   the humanized light chain variable region framework is from the light chain variable region framework of the R3.5H5G antibody provided that at least one position from the first group is occupied by the same amino acid present in the equivalent Position of the 1D10 immunoglobulin light chain variable region framework and provided that position L43 is occupied by the amino acid present in the equivalent position of a human kappa subgroup I consensus sequence;

the humanized heavy chain variable region framework is from the heavy chain region framework of the IC4 antibody provided at least one position selected from the second group is occupied by the same amino acid present in the equivalent position of the mouse 1D10immunoglobulin heavy chain variable region framework, and provided that position H73 is occupied by the same amino acid present in the equivalent position of a human immunoglobulin subgroup II or IV consensus sequence.

13. The humanized antibody of claim 12, wherein the humanized light chain comprises the amino acid sequence of FIG. 4A (upper) (SEQ ID NO. 1) and the humanized heavy chain comprises the amino acid sequence of FIG. 4B (upper) (SEQ ID NO. 3).

14. The humanized antibody of claim 13, wherein the humanized light chain further comprises a human kappa constant region, the humanized heavy chain further comprises a human γ1 constant region, and the humanized antibody effects ADCC and complement-mediated lysis of malignant B-cells when bound to a 28/32 kDa heterodimeric protein on the surface of the cells.

15. A humanized antibody, the antibody comprising a humanized heavy chain and a humanized light chain:

(1) the humanized light chain comprising three complementarity determining regions, CDR1, CDR2 and CDR3, of the mouse M291 immunoglobulin light chain, and a variable region framework from a human kappa light chain variable region framework sequence, and (2) the humanized heavy chain comprising three complementarity determining regions, CDR1, CDR2 and CDR3, of the mouse M291 immunoglobulin heavy chain, and a variable region framework from a human heavy chain variable region framework sequence provided that at least one position selected from a group consisting of H30, H67, H68, H70, H72 and H74 is occupied by the same amino acid present in the equivalent position of the mouse M291 immunoglobulin heavy chain variable region framework;

wherein the immunoglobulin specifically binds to a CD3 antigen on the surface of T cells with a binding affinity having a lower limit of about $10^7$ $M^{-1}$ and an upper limit of about five-times the binding affinity of the M291 immunoglobulin wherein the mouse antibody has an IgG1 heavy chain with a variable domain designated SEQ. ID. No. 11 and a kappa light chain with a variable domain designated SEQ. ID. No. 9.

16. The humanized antibody of claim 15, wherein the humanized light chain variable region framework is from the light chain variable region framework of the HF2-1/17 antibody; the humanized heavy chain region framework is from the heavy chain region variable framework of the 21/28 antibody provided that at least one position selected from the group is occupied by the same amino acid present in the equivalent position of the mouse M291 immunoglobulin heavy chain variable region framework, and provided that position 44 is occupied by the same amino acid present in the equivalent position of a human immunoglobulin subgroup I consensus sequence.

17. The humanized antibody of claim 16, wherein the humanized light chain comprises the amino acid sequence of FIG. 5A (upper) (SEQ ID NO. 8) and the humanized heavy chain comprises the amino acid sequence of FIG. 5B (upper) (SEQ ID NO. 10).

18. The bispecific antibody of claim 1 that is humanized.

19. The bispecific antibody of claim 18, wherein the first antigen is the CD3 antigen.

20. The bispecific antibody of claim 19, comprising:

a first binding fragment comprising:
a humanized form of the heavy chain variable region of the M291 antibody;
a humanized form of the light chain variable region of the M291 antibody; and a second binding fragment, which is linked to the first binding fragment, comprising:
a humanized form of the heavy chain variable region from the 1D10 antibody;
a humanized form of the light chain variable region from the 1D10 antibody;

wherein the first binding fragment specifically binds to the CD3 antigen and the second binding fragment specifically binds to the 28/32 kDa heterodimeric antigen on the surface of the malignant B cells wherein the mouse M291 antibody has a light chain variable domain designated SEQ. ID. No. 9 and a heavy chain variable domain designated SEQ. ID. No. 11.

21. The bispecific antibody of claim 20, wherein:

the humanized form of the heavy chain variable region of the M291 antibody comprises three complementarity determining regions, CDR1, CDR2 and CDR3, of M291 immunoglobulin heavy chain, and a variable region framework from a human heavy chain variable region framework sequence provided that at least one position selected from a group consisting of H30, H67, H68, H70, H72 and H74 is occupied by the same amino acid present in the equivalent position of the mouse M291 immunoglobulin heavy chain variable region framework;

the humanized form of the light chain variable region of the M291 antibody comprises three complementarity determining regions, CDR1, CDR2 and CDR3, of the M291 immunoglobulin light chain, and a variable region framework from a human kappa light chain variable region framework sequence;

the humanized form of the heavy chain variable region. from the 1D10 antibody comprises three complementarity determining regions, CDR1, CDR2 and CDR3, of 1D10 immunoglobulin heavy chain, and a variable region framework from a human heavy chain variable region framework sequence provided that at least one position selected from a second group consisting of H27, H29, H30, H37, H67, H71, H78 and H83 is occupied by the same amino acid present in the equivalent position of the mouse 1D10 immunoglobulin heavy chain variable region framework; and the humanized form of the light chain variable region from the 1D10 antibody comprises three complementarity determining regions, CDR1, CDR2 and CDR3, of the 1D10 immunoglobulin light chain, and a variable region framework from a human kappa light chain variable region framework sequence provided that at least one position selected from a first group consisting of L48, L49, L69, and L70 wherein the amino acid position is occupied by the same amino acid present in the equivalent position of the 1D10 immunoglobulin light chain variable region framework.

22. The bispecific antibody of claim 21, wherein the first binding fragment comprises the heavy chain variable region shown in FIG. 5B (upper) (SEQ ID NO. 10) and the light chain variable region shown in FIG. 5A (upper) (SEQ ID NO. 8), and the second binding fragment comprises the heavy chain variable region shown in FIG. 4B (upper) (SEQ ID NO. 3) and the light chain variable region shown in FIG. 4A (upper) (SEQ ID NO. 1).

23. The bispecific antibody of claim 22, wherein the first and second binding fragments each further comprises a segment of a constant region fused to the respective heavy chain variable regions, and the binding fragments are linked by association of the constant regions.

24. The bispecific antibody of claim 23, wherein the binding fragments are Fab or Fab'.

25. The bispecific antibody of claim 24, wherein the first and second binding fragments are Fab's and the bispecific antibody is a $F(ab')_2$.

26. The bispecific antibody of claim 25, wherein the first and second binding fragments further comprise first and second leucine zippers fused to the respective constant regions.

27. The bispecific antibody of claim 26, wherein the first binding fragment comprises a heavy chain having the amino acid sequence shown in FIG. 5D (SEQ ID NO. 13) and the second binding fragment comprises a heavy chain having the amino acid sequence shown in FIG. 4D (SEQ ID NO. 6).

28. A composition comprising the bispecific antibody of claim 1 and a pharmaceutically acceptable carrier.

* * * * *

UNITED STATES PATENT AND TRADEMARK OFFICE
CERTIFICATE OF CORRECTION

PATENT NO. : 6,129,914
DATED : October 10, 2000
INVENTOR(S) : Weiner et al.

It is certified that error appears in the above-identified patent and that said Letters Patent is hereby corrected as shown below:

Column 39,
Should read -- 4. The bispecific antibody of claim 3, wherein the bispecific antibody is produced by the cell line ATCC HB [1099.3] 10993. --

Column 40-41,
12. The humanized antibody of claim 11, wherein the humanized light chain variable region framework is from the light chain variable region framework of the R3.5H5G antibody provided that at least one position from the first group is occupied by the same amino acid present in the equivalent [Position] position of the 1D10 immunoglobulin light chain variable region framework and provided that position L43 is occupied by the amino acid present in the equivalent position of a human kappa subgroup I consensus sequence;
the humanized heavy chain region framework is from the heavy chain region framework of the IC4 antibody provided at least one position selected from the second group is occupied by the same amino acid present in the equivalent position of the mouse [1D10immunoglobulin] 1D10 immunoglobulin heavy chain variable region framework, and provided that position H73 is occupied by the same amino acid present in the equivalent position of a human immunoglobulin subgroup II or IV consensus sequence.

Signed and Sealed this

Twenty-third Day of October, 2001

Attest:

*Nicholas P. Godici*

NICHOLAS P. GODICI
*Attesting Officer*   Acting Director of the United States Patent and Trademark Office

UNITED STATES PATENT AND TRADEMARK OFFICE
CERTIFICATE OF CORRECTION

| | | |
|---|---|---|
| PATENT NO. | : 6,129,914 | Page 1 of 6 |
| APPLICATION NO. | : 08/397411 | |
| DATED | : October 10, 2000 | |
| INVENTOR(S) | : George Weiner et al. | |

It is certified that error appears in the above-identified patent and that said Letters Patent is hereby corrected as shown below:

Delete drawings sheets 3, 4, 5, and 6 substitute therefor the drawing sheets 3, 4, 5, and 6 as shown on the attached pages.

In the Sequence Listing:

At column 25, line 8, in SEQ ID NO:2, change
  "Glu Asp Phe Ala Thr Tyr Tyr Cys Gln His His Tyr Gly Asn Ser Tyr",
to -- Glu Asp Phe Gly Asn Tyr Tyr Cys Gln His His Tyr Gly Asn Ser Tyr --.

At column 25, line 48, in SEQ ID NO:4, change
  " Gly Val His Trp Val Arg Gln Ser Pro Gly Lys Gly Leu Glu Tip Ile",
to --Gly Val His Trp Val Arg Gln Ser Pro Gly Lys Gly Leu Glu Trp Leu--.

At column 33, line 14, in SEQ ID NO:8, change
  "Asp Ala Asp Thr Tyr Tyr Cys Gln Gln Trp Ser Ser Asn Pro Pro Thr",
to -- Asp Ala Ala Thr Tyr Tyr Cys Gln Gln Trp Ser Ser Asn Pro Pro Thr--.

At column 33, line 26, in SEQ ID NO:9, change
  "Asp Ile Val Leu Thr Gln Ser Pro Ala Ile Met Ser Ala Pro Gly",
to --Gln Ile Val Leu Thr Gin Ser Pro Ala Ile Met Ser Ala Pro Gly--.

At column 33, line 30, in SEQ ID NO:9, change
  "Asn Trp Tyr Gln Gln Lys Ser Gly Thr Ser Pro Lys Arg Trp Thr Tyr",
to --Asn Trp Tyr Lys Gln Lys Ser Gly Thr Ser Pro Lys Arg Trp Thr Tyr--.

At column 33, line 36, in SEQ ID NO:9, change
  "Asp Ala Asp Thr Tyr Tyr Cys Gln Gln Trp Ser Ser Asn Pro Pro Thr",
to --Asp Ala Ala Thr Tyr Tyr Cys Gln Gln Trp Ser Ser Asn Pm Pro Thr--,

UNITED STATES PATENT AND TRADEMARK OFFICE
CERTIFICATE OF CORRECTION

PATENT NO. : 6,129,914
APPLICATION NO. : 08/397411
DATED : October 10, 2000
INVENTOR(S) : George Weiner et al.

It is certified that error appears in the above-identified patent and that said Letters Patent is hereby corrected as shown below:

At column 39, line 36, in SEQ ID NO:13, change
  "Leu Gln Thr Glu Ile Ala Asn Leu Leu Lys Gly Lys Glu Lys Leu Glu",
to -- Leu Gln Thr Glu Ile Ala Asn Leu Leu Lys Glu Lys Glu Lys Leu Glu --, Signed and Sealed this Twenty-eighth Day of August, 2007

JON W. DUDAS
*Director of the United States Patent and Trademark Office*

| | | | | | | | | | | | | | | | | |
|---|---|---|---|---|---|---|---|---|---|---|---|---|---|---|---|---|
| 1 | | D | I | Q | M | T | Q | S | P | S | S | L | S | A | S | V | G | D | R | V | T |
| 21 | | I | T | C | S | A | S | S | S | V | S | Y | M | N | W | Y | Q | Q | K | P | G |
| 41 | | K | A | P | K | R | L | I | Y | D | T | S | K | L | A | S | G | V | P | S | R |
| 61 | | F | S | G | S | G | S | G | T | D | F | T | L | T | I | S | S | L | Q | P | E |
| 81 | | D | F | A | T | Y | Y | C | Q | Q | W | S | S | N | P | P | T | F | G | G | G |
| 101 | | T | K | V | E | I | K | R | T | V | A | A | P | S | V | F | I | F | P | P | S |
| 121 | | D | E | Q | L | K | S | G | T | A | S | V | V | C | L | L | N | N | F | Y | P |
| 141 | | R | E | A | K | V | Q | W | K | V | D | N | A | L | Q | S | G | N | S | Q | E |
| 161 | | S | V | T | E | Q | D | S | K | D | S | T | Y | S | L | S | S | T | L | T | L |
| 181 | | S | K | A | D | Y | E | K | H | K | V | Y | A | C | E | V | T | H | Q | G | L |
| 201 | | S | S | P | V | T | K | S | F | N | R | G | E | C |

FIG. 5C

| | | | | | | | | | | | | | | | | |
|---|---|---|---|---|---|---|---|---|---|---|---|---|---|---|---|---|
| 1 | | Q | V | Q | L | V | Q | S | G | A | E | V | K | K | P | G | A | S | V | K | V |
| 21 | | S | C | K | A | S | G | Y | T | F | I | S | Y | T | M | H | W | V | R | Q | A |
| 41 | | P | G | Q | G | L | E | W | M | G | Y | I | N | P | R | S | G | Y | T | H | Y |
| 61 | | N | Q | K | L | K | D | K | A | T | L | T | A | D | K | S | A | S | T | A | Y |
| 81 | | M | E | L | S | S | L | R | S | E | D | T | A | V | Y | Y | C | A | R | S | A |
| 101 | | Y | Y | D | Y | D | G | F | A | Y | W | G | Q | G | T | L | V | T | V | S | S |
| 121 | | A | S | T | K | G | P | S | V | F | P | L | A | P | S | S | K | S | T | S | G |
| 141 | | G | T | A | A | L | G | C | L | V | K | D | Y | F | P | E | P | V | T | V | S |
| 161 | | W | N | S | G | A | L | T | S | G | V | H | T | F | P | A | V | L | Q | S | S |
| 181 | | G | L | Y | S | L | S | S | V | V | T | V | P | S | S | S | L | G | T | Q | T |
| 201 | | Y | I | C | N | V | N | H | K | P | S | N | T | K | V | D | K | K | V | E | P |
| 221 | | K | S | C | D | K | T | H | T | C | P | P | C | K | C | P | A | G | G | L | T |
| 241 | | D | T | L | Q | A | E | T | D | Q | L | E | D | K | K | S | A | L | Q | T | E |
| 261 | | I | A | N | L | L | K | E | K | E | K | L | E | F | I | L | A | A | T | S |

FIG. 5D

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 107 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Ser Asn Ala Lys Thr Leu Ala Glu Gly Val Pro Ser Arg Phe Ser Gly
    50                  55                  60

Ser Gly Ser Gly Lys Gln Phe Thr Leu Thr Ile Ser Ser Leu Gln Pro
65                  70                  75                  80

Glu Asp Phe Ala Thr Tyr Tyr Cys Gln His His Tyr Gly Asn Ser Tyr
                85                  90                  95

Pro Phe Gly Gln Gly Thr Lys Leu Glu Ile Lys
            100                 105
```

(2) INFORMATION FOR SEQ ID NO:2:

(i) SEQUENCE CHARACTERISTICS:
      (A) LENGTH: 107 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
```

```
                20                  25                  30
Leu Ala Trp Tyr Gln Gln Lys Gln Gly Lys Ser Pro Gln Leu Leu Val
            35                  40                  45
Ser Asn Ala Lys Thr Leu Ala Glu Gly Val Thr Ser Arg Phe Ser Gly
 50                  55                  60
Ser Gly Ser Gly Lys Gln Phe Ser Leu Lys Ile Asn Ser Leu Gln Pro
 65                  70                  75                  80
Glu Asp Phe Ala Thr Tyr Tyr Cys Gln His His Tyr Gly Asn Ser Tyr
                85                  90                  95
Pro Phe Gly Gly Gly Thr Lys Leu Glu Ile Lys
                100                 105
```

(2) INFORMATION FOR SEQ ID NO:3:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Gln Val Gln Leu Gln Glu Ser Gly Pro Gly Leu Val Lys Pro Ser Glu
 1                   5                  10                  15
Thr Leu Ser Leu Thr Cys Thr Val Ser Gly Phe Ser Leu Thr Asn Tyr
                20                  25                  30
Gly Val His Trp Val Arg Gln Ser Pro Gly Lys Gly Leu Glu Trp Ile
            35                  40                  45
Gly Val Lys Trp Ser Gly Gly Ser Thr Glu Tyr Asn Ala Ala Phe Ile
        50                  55                  60
Ser Arg Leu Thr Ile Ser Lys Asp Thr Ser Lys Asn Gln Val Ser Leu
 65                  70                  75                  80
Lys Leu Asn Ser Leu Thr Ala Ala Asp Thr Ala Val Tyr Tyr Cys Ala
                85                  90                  95
Arg Asn Asp Arg Tyr Ala Met Asp Tyr Trp Gly Gln Gly Thr Leu Val
                100                 105                 110
Thr Val Ser Ser
        115
```

(2) INFORMATION FOR SEQ ID NO:4:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Gln Val Gln Leu Lys Gln Ser Gly Pro Gly Leu Val Gln Pro Ser Gln
 1                   5                  10                  15
Ser Leu Ser Ile Thr Cys Thr Gly Ser Gly Phe Ser Leu Thr Asn Tyr
                20                  25                  30
Gly Val His Trp Val Arg Gln Ser Pro Gly Lys Gly Leu Glu Trp Ile
            35                  40                  45
Gly Val Lys Trp Ser Gly Gly Ser Thr Glu Tyr Asn Ala Ala Phe Ile
        50                  55                  60
```

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Met Tyr Tyr Cys Ala
                85                  90                  95

Arg Asn Asp Arg Tyr Ala Met Asp Tyr Trp Gly Gln Gly Thr Ser Val
            100                 105                 110

Thr Val Ser Ser
        115

(2) INFORMATION FOR SEQ ID NO:5:

(i) SEQUENCE CHARACTERISTICS:
        (A) LENGTH: 214 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Ser Asn Ala Lys Thr Leu Ala Glu Gly Val Pro Ser Arg Phe Ser Gly
50                  55                  60

Ser Gly Ser Gly Lys Gln Phe Thr Leu Thr Ile Ser Ser Leu Gln Pro
65                  70                  75                  80

Glu Asp Phe Ala Thr Tyr Tyr Cys Gln His His Tyr Gly Asn Ser Tyr
                85                  90                  95

Pro Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

(2) INFORMATION FOR SEQ ID NO:6:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Asn Tyr
                 20                  25                  30

Gly Val His Trp Val Arg Gln Ser Pro Gly Lys Gly Leu Glu Trp Ile
                 35                  40                  45

Gly Val Lys Trp Ser Gly Gly Ser Thr Glu Tyr Asn Ala Ala Phe Ile
             50                  55                  60

Ser Arg Leu Thr Ile Ser Lys Asp Thr Ser Lys Asn Gln Val Ser Leu
 65                  70                  75                  80

Lys Leu Asn Ser Leu Thr Ala Ala Asp Thr Ala Val Tyr Tyr Cys Ala
                 85                  90                  95

Arg Asn Asp Arg Tyr Ala Met Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Lys Cys Pro Ala Gly Gly Arg Ile Ala Arg Leu Glu
225                 230                 235                 240

Glu Lys Val Lys Thr Leu Lys Ala Gln Asn Ser Glu Leu Ala Ser Thr
                245                 250                 255

Ala Asn Met Leu Arg Glu Gln Val Ala Gln Leu Lys Gln Lys Val Met
                260                 265                 270

Asn (2) INFORMATION FOR SEQ ID NO:7:

(i) SEQUENCE CHARACTERISTICS:
        (A) LENGTH: 446 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Asn Tyr
                 20                  25                  30

Gly Val His Trp Val Arg Gln Ser Pro Gly Lys Gly Leu Glu Trp Ile
                 35                  40                  45

Gly Val Lys Trp Ser Gly Gly Ser Thr Glu Tyr Asn Ala Ala Phe Ile
             50                  55                  60
```

```
Ser Arg Leu Thr Ile Ser Lys Asp Thr Ser Lys Asn Gln Val Ser Leu
 65                  70                  75                  80

Lys Leu Asn Ser Leu Thr Ala Ala Asp Thr Ala Val Tyr Tyr Cys Ala
                 85                  90                  95

Arg Asn Asp Arg Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

(2) INFORMATION FOR SEQ ID NO:8:

(i) SEQUENCE CHARACTERISTICS:
        (A) LENGTH: 106 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:8:

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Asp Thr Tyr Tyr Cys Gln Gln Trp Ser Ser Asn Pro Pro Thr
                85                  90                  95

Phe Gly Gly Gly Thr Lys Val Glu Ile Lys
                100                 105
```

(2) INFORMATION FOR SEQ ID NO:9:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Asp Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Thr Tyr
            35                  40                  45

Asp Thr Ser Lys Leu Ala Ser Gly Val Pro Ala Arg Phe Ser Gly Ser
            50                  55                  60

Gly Ser Gly Thr Ser Tyr Ser Leu Thr Ile Ser Ser Met Glu Ala Glu
65                  70                  75                  80

Asp Ala Asp Thr Tyr Tyr Cys Gln Gln Trp Ser Ser Asn Pro Pro Thr
                85                  90                  95

Phe Gly Ser Gly Thr Lys Leu Glu Ile Lys
                100                 105
```

(2) INFORMATION FOR SEQ ID NO:10:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30
```

```
Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
 50                  55                  60

Lys Asp Lys Ala Thr Leu Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Tyr Tyr Asp Tyr Asp Gly Phe Ala Tyr Trp Gly Gln
                100                 105                 110

Gly Thr Leu Val Thr Val Ser Ser
            115                 120

(2) INFORMATION FOR SEQ ID NO:11:

(i) SEQUENCE CHARACTERISTICS:
         (A) LENGTH: 120 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:11:

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Ile Ser Tyr
                 20                  25                  30

Thr Met His Trp Val Lys Gln Arg Pro Gly Gln Gly Leu Glu Trp Ile
         35                  40                  45

Gly Tyr Ile Asn Pro Arg Ser Gly Tyr Thr His Tyr Asn Gln Lys Leu
 50                  55                  60

Lys Asp Lys Ala Thr Leu Thr Ala Asp Lys Ser Ser Ser Ser Ala Tyr
 65                  70                  75                  80

Met Gln Leu Ser Ser Leu Thr Ser Glu Asp Ser Ala Val Tyr Tyr Cys
                 85                  90                  95

Ala Arg Ser Ala Tyr Tyr Asp Tyr Asp Gly Phe Ala Tyr Trp Gly Gln
                100                 105                 110

Gly Thr Leu Val Thr Val Ser Ala
            115                 120

(2) INFORMATION FOR SEQ ID NO:12:

(i) SEQUENCE CHARACTERISTICS:
         (A) LENGTH: 213 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:12:

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Val Ser Tyr Met
                 20                  25                  30

Asn Trp Tyr Gln Gln Lys Pro Gly Lys Ala Pro Lys Arg Leu Ile Tyr
                 35                  40                  45

Asp Thr Ser Lys Leu Ala Ser Gly Val Pro Ser Arg Phe Ser Gly Ser
```

```
                50                  55                  60
Gly Ser Gly Thr Asp Phe Thr Leu Thr Ile Ser Ser Leu Gln Pro Glu
65                  70                  75                  80

Asp Phe Asp Thr Tyr Tyr Cys Gln Gln Trp Ser Ser Asn Pro Pro Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
                130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

(2) INFORMATION FOR SEQ ID NO:13:

(i) SEQUENCE CHARACTERISTICS:
        (A) LENGTH: 279 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
                20                  25                  30

Thr Met His Trp Val Arg Gln Ala Pro Gly Gln Gly Leu Glu Trp Met
                35                  40                  45

Gly Tyr Ile Asn Pro Arg Ser Gly Tyr Thr His Tyr Asn Gln Lys Leu
50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

-continued

```
                      180                 185                 190
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Lys Cys Pro Ala Gly Gly Leu Thr
225                 230                 235                 240

Asp Thr Leu Gln Ala Glu Thr Asp Gln Leu Glu Asp Lys Lys Ser Ala
                245                 250                 255

Leu Gln Thr Glu Ile Ala Asn Leu Leu Lys Gly Lys Glu Lys Leu Glu
                260                 265                 270

Phe Ile Leu Ala Ala Thr Ser
        275

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Leu Xaa Xaa Xaa Xaa Xaa Xaa
1               5
```